United States Patent
Bhirud et al.

(10) Patent No.: US 9,670,160 B2
(45) Date of Patent: Jun. 6, 2017

(54) PROCESS FOR THE PREPARATION OF TOFACITINIB AND INTERMEDIATES THEREOF

(71) Applicant: Glenmark Pharmaceuticals Limited, Mumbai (IN)

(72) Inventors: Shekhar Bhaskar Bhirud, Mumbai (IN); Sushanta Mishra, Bolangir (IN); Suresh Babu Narayanan, Thane (IN); Sachin Bhagwan Naykodi, Navi Mumbai (IN); Abhijit Ajaysinh Pardeshi, Pune (IN); Ashu Dhiman, Muzaffarnagar (IN); Samir Naik, Thane (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 14/655,947

(22) PCT Filed: Dec. 27, 2013

(86) PCT No.: PCT/IN2013/000808
§ 371 (c)(1),
(2) Date: Jun. 26, 2015

(87) PCT Pub. No.: WO2014/102826
PCT Pub. Date: Jul. 3, 2014

(65) Prior Publication Data
US 2015/0336961 A1    Nov. 26, 2015

Related U.S. Application Data

(60) Provisional application No. 61/768,952, filed on Feb. 25, 2013.

(30) Foreign Application Priority Data

Dec. 28, 2012 (IN) .................. 3684/MUM/2012
May 24, 2013 (IN) .................. 1845/MUM/2013

(51) Int. Cl.
C07D 487/04    (2006.01)
C07D 211/56    (2006.01)

(52) U.S. Cl.
CPC .......... *C07D 211/56* (2013.01); *C07D 487/04* (2013.01)

(58) Field of Classification Search
CPC ........................ C07D 487/04; C07D 211/56
See application file for complete search history.

(56) References Cited

U.S. PATENT DOCUMENTS 7,301,023 B2    11/2007  Flanagan et al.
8,232,394 B2    7/2012   Ruggeri et al.

FOREIGN PATENT DOCUMENTS

| WO | 03048162 A1 | 6/2003 |
| WO | 2005060972 A2 | 7/2005 |
| WO | 2007012953 A2 | 2/2007 |
| WO | 2010014930 A2 | 2/2010 |
| WO | 2010123919 A2 | 10/2010 |

OTHER PUBLICATIONS

Demirtas et al., 2002, http://www.mdpi.org/ecsoc/ecsoc-6/Papers/A019/A019_files/index3.htm.*
Demirtas et al. date, 2002, http://www.mdpi.net/ecsoc-6/index.htm.*

* cited by examiner

*Primary Examiner* — Sun Jae Yoo
(74) *Attorney, Agent, or Firm* — Ryan, Mason & Lewis, LLP

(57) ABSTRACT

The present invention relates to process for the preparation of tofacitinib and intermediates thereof.

20 Claims, No Drawings

PROCESS FOR THE PREPARATION OF TOFACITINIB AND INTERMEDIATES THEREOF

PRIORITY

This application claims priority under 35 U.S.C. §371 to International Application No. PCT/IN2013/000808, filed Dec. 27, 2013 which claims the benefit under 35 U.S.C. §119 to Indian Provisional Application No. 3684/MUM2012, filed on Dec. 28, 2012; U.S. Provisional Application No. 61/768,952 filed on Feb. 25, 2013 and Indian Provisional Application No. 1845/MUM/2013 filed on May 24, 2013, all entitled "PROCESS FOR PREPARATION OF TOFACITINIB AND INTERMEDIATES THEREOF", the contents of which are incorporated herein by reference.

FIELD OF THE INVENTION

The present invention relates to a novel process preparation of tofacitinib and its salts.

BACKGROUND OF THE INVENTION

Tofacitinib, chemically known as (3R,4R)-4-methyl-3-(methyl-7H-pyrrolo[2,3-d]pyrimidin-4-ylamino)-β-oxo-1-piperidinepropanenitrile, is represented Formula I. Tofacitinib citrate, a janus kinase inhibitor, is approved as XELJANZ® tablets for treatment of rheumatoid arthritis.

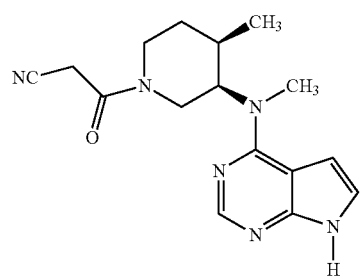

I

Various intermediates and processes for preparation of tofacitinib are disclosed in patents like U.S. Pat. No. 7,301,023 and U.S. Pat. No. 8,232,394. The prior art processes are time consuming, tedious and laborious. The ensuing product obtained in these processes may contain impurities, the separation and removal of which pose as a challenge, which may require multiple purification steps thereby reducing the product yield.

Presently, we have developed a novel process and novel intermediates for preparation of tofacitinib and salts thereof.

SUMMARY OF THE INVENTION

The present invention provides a compound of Formula IVA in the form of racemates, enantiomers, diastereomers or mixtures thereof; and salts thereof

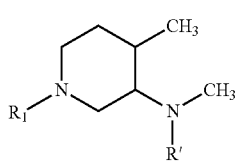

IVA wherein, $R_1$ may be selected from the group consisting of hydrogen and trityl; R' may be hydrogen or a group represented by Formula Y

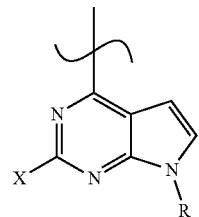

Y wherein X is a halogen and R may be selected from the groups consisting of hydrogen, benzyl, tosyl, tertiary-butyloxy carbonyl and carbobenzyloxy; with the proviso that both $R_1$ and R' can not be hydrogen at the same time.

The present invention provides a process for preparation of compound of Formula V-I in the form of racemates, enantiomers, diastereomers or mixtures thereof; and salts thereof

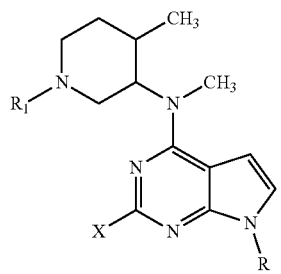

V-I wherein, $R_1$ may be selected from the group consisting of hydrogen, trityl, benzyl and substituted benzyl wherein substituents on benzyl group may be selected from lower alkyl, lower alkoxy, nitro, halo and amino; R may be selected from the groups consisting of hydrogen, benzyl, tosyl, tertiary-butyloxy carbonyl and carbobenzyloxy; and X is a halogen; the process comprising, (a) reacting a compound of Formula IVA wherein $R_1$ may be selected from the group consisting of trityl, benzyl and substituted benzyl wherein substituents on benzyl group may be selected from lower alkyl, lower alkoxy, nitro, halo and amino; and R' is H,

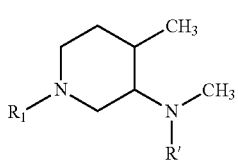

IVA with a compound of Formula III-I wherein R may be selected from the group consisting of benzyl, tosyl, tertiary-butyloxy carbonyl and carbobenzyloxy; and X is a halogen

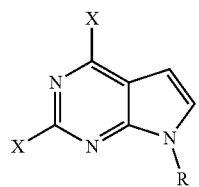

III-I to form a compound of Formula V-I wherein $R_1$ may be selected from the group consisting of trityl, benzyl and substituted benzyl wherein substituents on benzyl group may be selected from lower alkyl, lower alkoxy, nitro, halo and amino; and R may be selected from the group consisting of benzyl, tosyl, tertiary-butyloxy carbonyl and carbobenzyloxy; and X is a halogen; and (b) optionally, deprotecting the compound of Formula V-I obtained in step (a) to form a compound of Formula V-I wherein at least one of R or $R_1$ is hydrogen; and X is a halogen The present invention provides a process for the preparation of a compound of Formula V-II wherein, $R_1$ may be selected from the group consisting of hydrogen, trityl, benzyl and substituted benzyl wherein substituents on benzyl group may be selected from lower alkyl, lower alkoxy, nitro, halo and amino; R may be selected from the groups consisting of hydrogen, benzyl, tosyl, tertiary-butyloxy carbonyl and carbobenzyloxy; and X is a halogen;

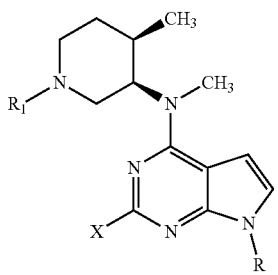

V-II the process comprising (a) reacting the compound of Formula IV wherein $R_1$ may be selected from the group consisting of trityl, benzyl and substituted benzyl wherein substituents on benzyl group may be selected from lower alkyl, lower alkoxy, nitro, halo and amino;

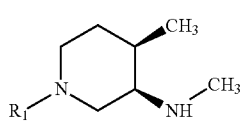

IV with a compound of Formula III-I wherein X is a halogen and R may be selected from the group consisting of benzyl, tosyl, tertiary-butyloxy carbonyl and carbobenzyloxy,

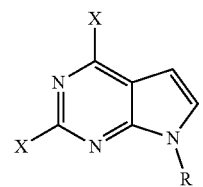

III-I to form a compound of formula V-II wherein $R_1$ may be selected from the group consisting of trityl, benzyl and substituted benzyl wherein substituents on benzyl group may be selected from lower alkyl, lower alkoxy, nitro, halo and amino; R may be selected from the groups consisting of hydrogen, benzyl, tosyl, tertiary-butyloxy carbonyl and carbobenzyloxy; and X is a halogen; and

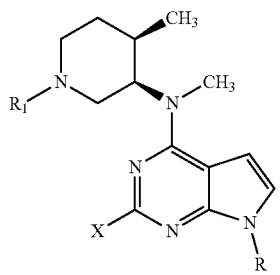

V-II (b) optionally, deprotecting the compound of Formula V-II so obtained to form a compound of Formula V-II wherein at least one of R or $R_1$ is hydrogen and X is a halogen.

The present invention provides a process for preparation of compound of formula V-II wherein each of R and $R_1$ is hydrogen; and X is a halogen

V-II from a compound of Formula V-II wherein $R_1$ is trityl; R is tosyl; and X is a halogen; the process comprising
a) sequentially detritylating and detosylating in either order the compound of formula V-II wherein $R_1$ is trityl; R is tosyl and X is a halogen into a compound of formula V-II wherein each of R and $R_1$ is hydrogen and X is a halogen; or
b) detritylating and detosylating in a single step the compound of formula V-II wherein $R_1$ is trityl; R is tosyl and X is a halogen into a compound of formula V-II wherein each of R and $R_1$ is hydrogen and X is a halogen, in a single step.

The present invention provides a process for the preparation of a compound of Formula IV and salts thereof;

wherein $R_1$ may be selected from the group consisting of trityl, 4-methoxybenzyl and 3,4-dimethoxybenzyl

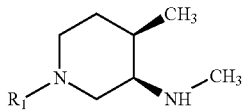

IV comprising
(a) converting a compound of Formula XIV to a compound of formula XV-I wherein $R_1$ may be selected from the group consisting of trityl, 4-methoxybenzyl and 3,4-dimethoxybenzyl

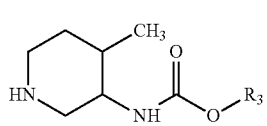

XIV

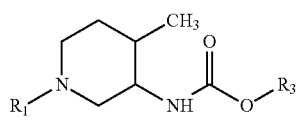

XV-I (b) converting the compound of Formula XV-I so obtained to a compound of Formula XVI-I; followed by

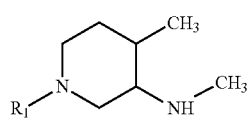

XVI-I (c) resolution of compound of Formula XVI-I so obtained.

The present invention provides use of
a. a compound of Formula IVA

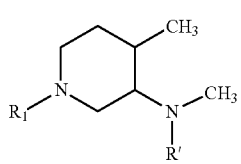

IVA wherein, $R_1$ may be selected from the group consisting of hydrogen and trityl; R' may be hydrogen or a group represented by Formula Y

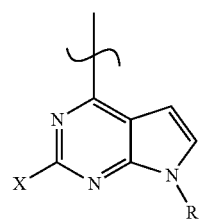

Y wherein X is a halogen and R may be selected from the groups consisting of hydrogen and tosyl; with the proviso that both $R_1$ and R' can not be hydrogen at the same time; or b. a compound of Formula V-I wherein $R_1$ may be hydrogen or trityl; R may be hydrogen or tosyl and X is a halogen; or

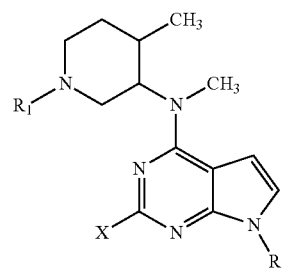

V-I c. a compound of Formula V wherein $R_1$ may be hydrogen or trityl and R may be hydrogen or tosyl; or

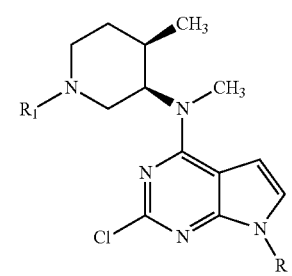

V d. a compound of Formula IV wherein $R_1$ is trityl

IV for the preparation of tofacitinib or salts thereof.

The present invention provides a process for purification of tofacitinib monocitrate by a process comprising recrystallization of tofacitinib monocitrate from a mixture of acetonitrile and water.

DETAILED DESCRIPTION OF THE INVENTION

Throughout this application tofacitinib citrate and tofacitinib monocitrate are used interchangeably.

Throughout this application tofacitinib, tofacitinib base and tofacitinib free base are used interchangeably.

The present invention provides a process for preparation of tofacitinib, a compound of Formula I and salts thereof comprising a process as depicted in scheme 1.

Scheme 1

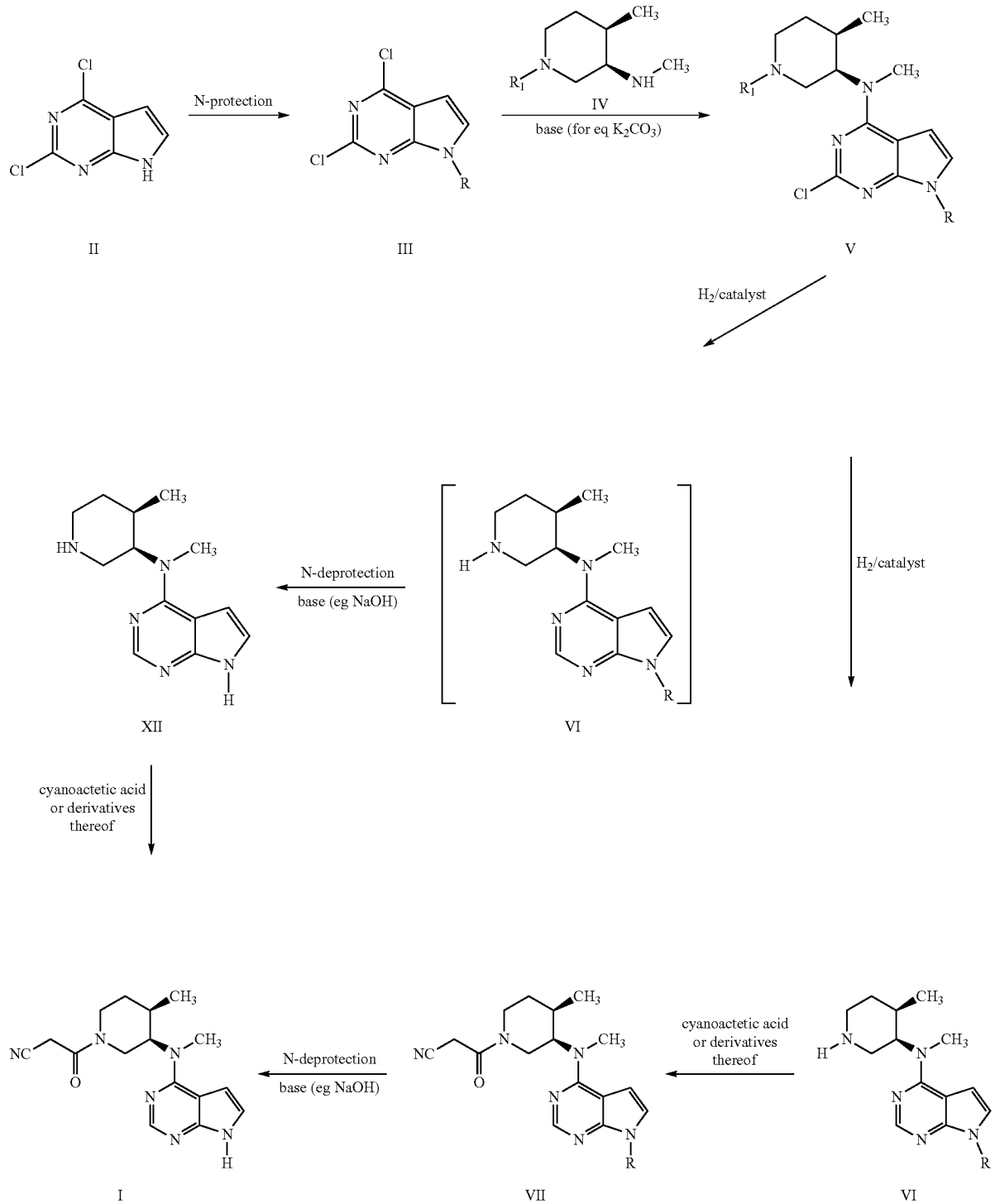

In scheme 1 depicted immediately above, R may be hydrogen or a nitrogen protecting group selected from the group consisting of benzyl, tosyl, tertiary-butyloxy carbonyl and carbobenzyloxy.

In scheme 1 depicted immediately above, $R_1$ may be hydrogen or a nitrogen protecting group selected from the group consisting of trityl, substituted benzyl wherein the substituents on the benzyl group are selected from the group consisting of halo, nitro, amino, lower alkyl and lower alkoxy groups.

In one embodiment, the present invention provides a process for preparation of tofacitinib, a compound of Formula I, and salts thereof comprising a process as depicted in scheme 1 A.

Scheme 1A

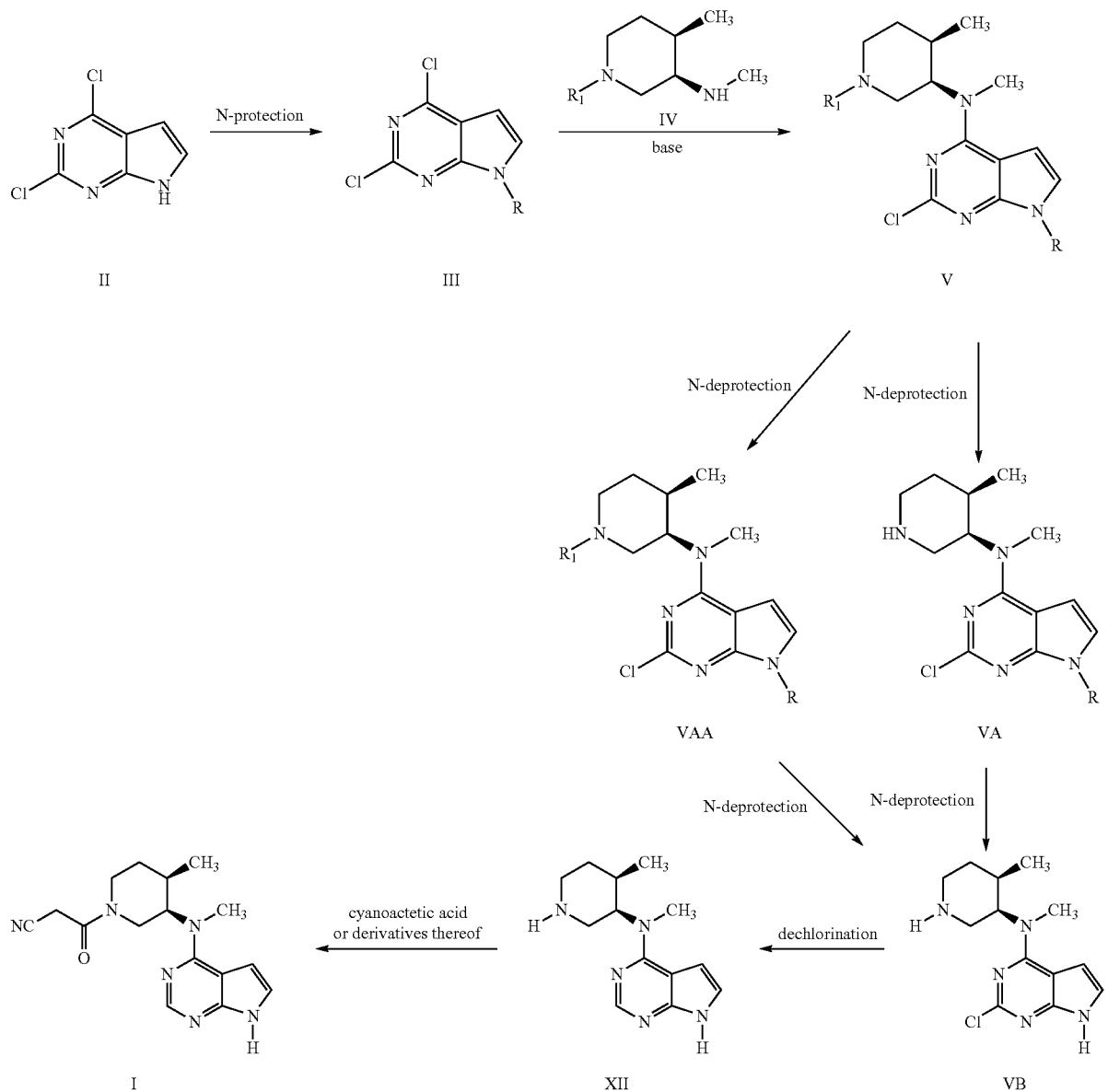

In scheme 1A depicted immediately above, R may be hydrogen or a nitrogen protecting group selected from the group consisting of benzyl, tosyl, tertiary-butyloxy carbonyl and carbobenzyloxy.

In scheme 1A depicted immediately above, R1 may be hydrogen or a nitrogen protecting group selected from the group consisting of trityl, substituted benzyl wherein the substituents on the benzyl group are selected from the group consisting of halo, nitro, amino, lower alkyl and lower alkoxy groups.

The substituents on benzyl group may be present on one or more than one positions.

The lower alkyl groups may be straight or branched chain C1-5 alkyl groups which may be methyl, ethyl, isopropyl, n-propyl and the like. The lower alkoxy groups may be straight or branched chain C1-5 alkoxy groups like methoxy, ethoxy, n-propoxy, isopropoxy and like. In one embodiment, the present invention provides a compound of Formula IVA in the form of racemates, enantiomers, diastereomers or mixtures thereof; and alts thereof

IVA wherein, $R_1$ may be selected from the group consisting of hydrogen, trityl, substituted benzyl wherein the substituents are selected from halo, nitro, amino, lower alkyl and lower alkoxy groups; R' may be hydrogen or a group represented by Formula Y

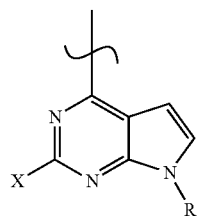

wherein X is a halogen and R may be selected from the groups consisting of hydrogen, benzyl, tosyl, tertiary-butyloxy carbonyl and carbobenzyloxy; with the proviso that both $R_1$ and R' can not be hydrogen at the same time.

The present invention is meant to encompass racemates and isomeric forms of compounds. Some of the compounds of the present invention have at least one asymmetric centre. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using enantiomerically pure acid or base. The diastereomeric derivatives may then be converted to the pure enantiomers by cleavage of the added chiral residue. The racemic mixtures of the compounds can also be separated directly by chromatographic methods using chiral stationary phases, which are well known in the art. Alternatively, any enantiomer of a compound may be obtained by stereoselective synthesis using optically pure starting materials or reagents of known configuration by methods known in the art.

In one embodiment, the present invention provides a compound of Formula IVA in the form of racemates, enantiomers, diastereomers or mixtures thereof; and salts thereof wherein $R_1$ may be selected from the group consisting of hydrogen, trityl, 4-methoxybenzyl and 3,4-dimethoxybenzyl; R' may be hydrogen or a group represented by Formula Y wherein X is a halogen and R may be selected from the groups consisting of hydrogen and tosyl with the proviso that both $R_1$ and R' can not be hydrogen at the same time.

In one embodiment, the present invention provides a compound of Formula IVA in the form of racemates, enantiomers, diastereomers or mixtures thereof; and salts thereof

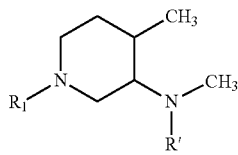

IVA wherein, $R_1$ may be selected from the group consisting of hydrogen and trityl; R' may be hydrogen or a group represented by Formula Y

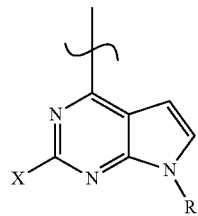

Y wherein X is a halogen and R may be selected from the groups consisting of hydrogen, benzyl, tosyl, tertiary-butyloxy carbonyl and carbobenzyloxy; with the proviso that both $R_1$ and R' can not be hydrogen at the same time.

In one embodiment, the present invention provides a compound of Formula IVA, described above, in the form of racemates, enantiomers, diastereomers or mixtures thereof; and salts thereof wherein, R1 may be selected from the group consisting of hydrogen and trityl; R' may be hydrogen or a group represented by Formula Y, as defined above, wherein X is a halogen and R may be selected from the groups consisting of hydrogen and tosyl; with the proviso that both $R_1$ and R' can not be hydrogen at the same time.

In one embodiment, the present invention provides a compound of Formula IVA, described above, wherein R' is hydrogen and $R_1$ is trityl; in the form of racemates, enantiomers, diastereomers or mixtures thereof; and salts thereof.

In one embodiment, the present invention provides a compound of Formula IVA, represented by Formula XVII

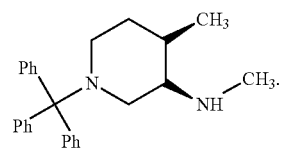

XVII

In one embodiment, the present invention provides a compound of Formula IVA, represented by Formula V-I; in the form of racemates, enantiomers, diastereomers or mixtures thereof; and salts thereof

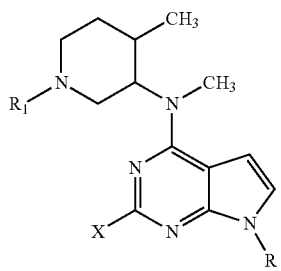

V-I wherein, $R_1$ may be selected from the group consisting of hydrogen, trityl, substituted benzyl wherein the substituents are selected from halo, nitro, amino, lower alkyl and lower alkoxy groups; X is a halogen; and R may be selected from the groups consisting of hydrogen, benzyl, tosyl, tertiary-butyloxy carbonyl and carbobenzyloxy.

In one embodiment, the present invention provides a compound of Formula V-I, wherein R₁ may be selected from the group consisting of hydrogen and trityl; X is a halogen and R may be selected from the groups consisting of hydrogen, benzyl, tosyl, tertiary-butyloxy carbonyl and carbobenzyloxy; in the form of racemates, enantiomers, diastereomers or mixtures thereof; and salts thereof.

In one embodiment, the present invention provides a compound of Formula V-I, described above, wherein R₁ may be hydrogen or trityl; R may be hydrogen or tosyl and X is chlorine; in the form of racemates, enantiomers, diastereomers or mixtures thereof; and salts thereof.

In one embodiment, the present invention provides a compound of Formula V-I, described above, represented by Formula V in scheme 1 and 1A,

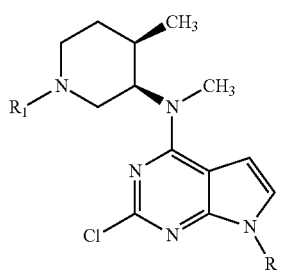

V wherein R₁ may be selected from the group consisting of hydrogen, trityl, substituted benzyl wherein the substituents are selected from halo, nitro, amino, lower alkyl and lower alkoxy groups and R may be selected from the groups consisting of hydrogen, benzyl, tosyl, tertiary-butyloxy carbonyl and carbobenzyloxy.

In one embodiment, the present invention provides a compound of Formula V, as depicted in scheme 1 and 1A, wherein R₁ may be hydrogen or trityl and R may be hydrogen or tosyl.

In one embodiment, the present invention provides a compound of Formula V, as depicted in scheme 1 and 1A, wherein R₁ is trityl and R is tosyl.

In one embodiment, the present invention provides a compound of Formula V, as depicted in scheme 1 and 1A, wherein R₁ is trityl and R is tertiary-butyloxy carbonyl.

In one embodiment, the present invention provides a compound of Formula V, as depicted in scheme 1 and 1A, wherein R₁ is trityl and R is hydrogen.

In one embodiment, the present invention provides a compound of Formula V, wherein R₁ is hydrogen and R is tosyl.

In one embodiment, the present invention provides a compound of Formula V, wherein both R and R₁ are hydrogen, as depicted by Formula VB in scheme 1A

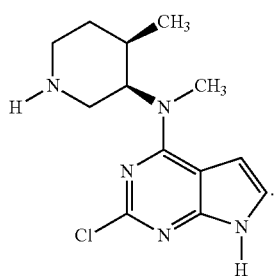

VB

In one embodiment, the present invention provides a compound of Formula V, as depicted in scheme 1A by formula VA,

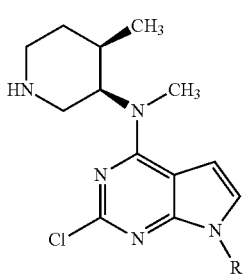

VA wherein R may be selected from the groups consisting of hydrogen, benzyl, tosyl, tertiary-butyloxy carbonyl and carbobenzyloxy.

In one embodiment, the present invention provides a compound of Formula VA, as depicted in scheme 1A, wherein R is tosyl.

In one embodiment, the present invention provides a compound of Formula VA, as depicted in scheme 1A, wherein R is tertiary-butyloxy carbonyl In one embodiment, the present invention provides a process for preparation of compound of Formula V-I in the form of racemates, enantiomers, diastereomers or mixtures thereof; and salts thereof

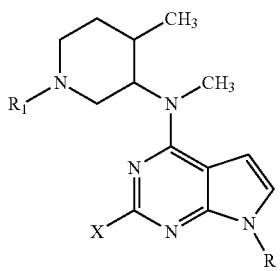

V-I wherein, R₁ may be selected from the group consisting of hydrogen, trityl, benzyl and substituted benzyl wherein substituents on benzyl group may be selected from lower alkyl, lower alkoxy, nitro, halo and amino; R may be selected from the groups consisting of hydrogen, benzyl, tosyl, tertiary-butyloxy carbonyl and carbobenzyloxy; and X is a halogen; the process comprising, (a) reacting a compound of Formula IVA wherein R₁ may be selected from the group consisting of trityl, benzyl and substituted benzyl wherein substituents on benzyl group may be selected from lower alkyl, lower alkoxy, nitro, halo and amino; and R' is H,

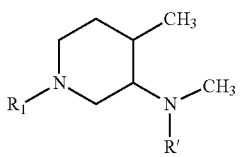

IVA with a compound of Formula III-I wherein R may be selected from the group consisting of benzyl, tosyl, tertiary-butyloxy carbonyl and carbobenzyloxy; and X is a halogen

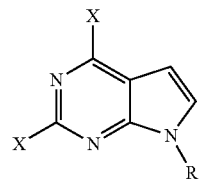

III-I to form a compound of Formula V-I wherein $R_1$ may be selected from the group consisting of trityl, benzyl and substituted benzyl wherein substituents on benzyl group may be selected from lower alkyl, lower alkoxy, nitro, halo and amino; and R may be selected from the group consisting of benzyl, tosyl, tertiary-butyloxy carbonyl and carbobenzyloxy; and X is a halogen and (b) optionally, deprotecting the compound of Formula V-I obtained in step (a) to form a compound of Formula V-I wherein at least one of R or $R_1$ is hydrogen.

In one embodiment, in step (a) as described above, in compound of Formula IVA $R_1$ may be trityl, 4-methoxybenzyl or 3,4-dimethoxybenzyl, preferably trityl; and R' is H; and in compound of Formula III-I, X is chlorine; and R may be tosyl or tert-butoxycarbonyl, preferably tosyl.

Step (a) as described above, may be performed in the presence of a base. The base used may be an inorganic or organic base. The inorganic base may include an alkali or alkaline earth metal hydroxide, an alkali or alkaline earth metal carbonate and the like, for example sodium hydroxide, potassium hydroxide, sodium carbonate, potassium carbonate and the like. The organic base may include an amine which may be a primary, secondary or a tertiary amine. Examples of organic base include methylamine, ethylamine, triethylamine, propylamine, isopropylamine, diisopropylamine, tertiary butylamine and the like. An organic base may also include pyridine and 1,8-Diazabicyclo[5.4.0]undec-7-ene (DBU).

Step (a) as described above, may be performed in the presence of a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof.

Deprotection in step (b), described above, comprises a)
  i. converting the compound of formula V-I, wherein $R_1$ may be selected from the group consisting of trityl, benzyl and substituted benzyl wherein substituents on benzyl group may be selected from lower alkyl, lower alkoxy, nitro, halo and amino, preferably $R_1$ may be trityl; R may be selected from the groups consisting of benzyl, tosyl, tertiary-butyloxy carbonyl and carbobenzyloxy; and X is a halogen, into a compound of Formula V-I wherein $R_1$ may be selected from the group consisting of trityl, benzyl and substituted benzyl wherein substituents on benzyl group may be selected from lower alkyl, lower alkoxy, nitro, halo and amino; R is hydrogen and X is a halogen; followed by
  ii. converting the compound of formula V-I so obtained into a compound of Formula V-I wherein each of R and R1 is hydrogen; or b)
  i. converting the compound of formula V-I, wherein $R_1$ may be selected from the group consisting of trityl, benzyl and substituted benzyl wherein substituents on benzyl group may be selected from lower alkyl, lower alkoxy, nitro, halo and amino; R may be selected from the groups consisting of benzyl, tosyl, tertiary-butyloxy carbonyl and carbobenzyloxy; and X is a halogen, into a compound of Formula V-I wherein $R_1$ is hydrogen; R may be selected from the groups consisting of benzyl, tosyl, tertiary-butyloxy carbonyl and carbobenzyloxy and X is a halogen, followed by
  ii. conversion of the compound of formula V-I so obtained into a compound of Formula V-I wherein each of R and R1 is hydrogen and X is a halogen; or c) converting compound of formula V-I, wherein $R_1$ may be selected from the group consisting of trityl, benzyl and substituted benzyl wherein substituents on benzyl group may be selected from lower alkyl, lower alkoxy, nitro, halo and amino; R may be selected from the groups consisting of benzyl, tosyl, tertiary-butyloxy carbonyl and carbobenzyloxy; and X is a halogen, directly into a compound of Formula V-I wherein each of R and $R_1$ is hydrogen and X is a halogen, in a single step.

In one embodiment, deprotection in step (b) as described above, involves deprotection of compound of Formula V-I wherein, $R_1$ may be trityl, 4-methoxybenzyl or 3,4-dimethoxybenzyl, preferably trityl; R may be tosyl or tert-butoxycarbonyl, preferably tosyl and X is chlorine.

In one embodiment, deprotection in a) i, described above, is performed using a base and deprotection in a) ii, described above, is performed using an acid or by hydrogenation.

Base used in a) i may be an inorganic or organic base as discussed supra.

a) i may be performed in the presence of a suitable solvent. The suitable solvents are as discussed supra.

Acid used in a) ii may be an organic or inorganic acid. The organic acid used may include an acid such as formic acid, acetic acid, citric acid, tartaric acid, bitartaric acid, benzoic acid, lactic acid, malic acid, fumaric acid, succinic acid, gluconic acid, pamoic acid, methanesulfonic acid, benzenesulfonic acid and the like. The inorganic acid used may include an acid such as hydrochloric acid, hydrobromic acid, hydroiodic acid, nitric acid, phosphoric acid, sulfuric acid, trifluoroacetic acid, and the like.

The hydrogenation as described in a) ii may be performed in the presence of a catalyst. The catalyst used may include metal catalysts such as platinum on carbon, palladium on carbon and the like; palladium hydroxide on carbon; platinum hydroxide on carbon; platinum oxide or raney nickel.

a) ii may be performed in the presence of a suitable solvent. The suitable solvents are as discussed supra:

In one embodiment, deprotection in b) i, described above, is performed using an acid or by hydrogenation and deprotection in a) ii, described above, is performed using a base.

Acid used in b) i may be an organic or inorganic acid as discussed supra.

The hydrogenation as described in b) i may be performed in the presence of a catalyst. The catalysts used for hydrogenation are as discussed supra.

b) i may be performed in the presence of a suitable solvent. The suitable solvents are as discussed supra.

Base used b) ii in may be an inorganic or organic base as discussed supra.

In one embodiment, deprotection in c), described above, may be performed using a base or an acid or by hydrogenation.

In one embodiment, the present invention provides a process for the preparation of a compound of Formula V-II wherein, $R_1$ may be selected from the group consisting of hydrogen, trityl, benzyl and substituted benzyl wherein substituents on benzyl group may be selected from lower alkyl, lower alkoxy, nitro, halo and amino; R may be selected from the groups consisting of hydrogen, benzyl, tosyl, tertiary-butyloxy carbonyl and carbobenzyloxy; and X is a halogen;

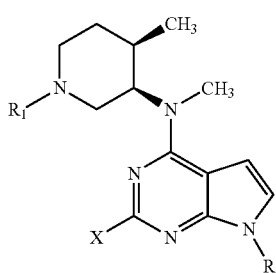

V-II the process comprising (a) reacting the compound of Formula IV wherein $R_1$ may be selected from the group consisting of trityl, benzyl and substituted benzyl wherein substituents on benzyl group may be selected from lower alkyl, lower alkoxy, nitro, halo and amino;

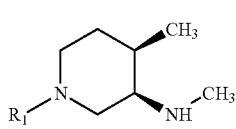

IV with a compound of Formula III-I wherein X is a halogen and R may be selected from the group consisting of benzyl, tosyl, tertiary-butyloxy carbonyl and carbobenzyloxy,

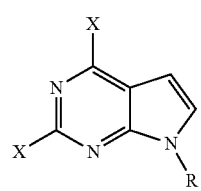

III-I to form a compound of formula V-II wherein $R_1$ may be selected from the group consisting of trityl, benzyl and substituted benzyl wherein substituents on benzyl group may be selected from lower alkyl, lower alkoxy, nitro, halo and amino; R may be selected from the groups consisting of hydrogen, benzyl, tosyl, tertiary-butyloxy carbonyl and carbobenzyloxy; and X is a halogen; and

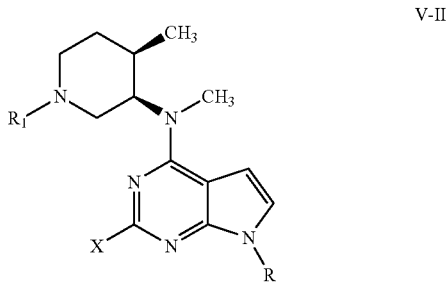

V-II (b) optionally, deprotecting the compound of Formula V-II so obtained to form a compound of Formula V-II wherein at least one of R or $R_1$ is hydrogen and X is a halogen.

Step (a) as described above may be performed in the presence of a base. Base used may be an organic or inorganic base as discussed supra. Preferred inorganic bases include potassium carbonate, sodium carbonate and sodium hydroxide. Preferred organic bases include triethylamine and diisopropylamine.

Step (a) as described above may be performed in the presence of a suitable solvent. The suitable solvents are as discussed supra.

Deprotection in step (b), described above, comprises a)
  i. converting the compound of formula V-II, wherein $R_1$ may be selected from the group consisting of trityl, benzyl and substituted benzyl wherein substituents on benzyl group may be selected from lower alkyl, lower alkoxy, nitro, halo and amino; R may be selected from the groups consisting of benzyl, tosyl, tertiary-butyloxy carbonyl and carbobenzyloxy; and X is a halogen, into a compound of Formula V-II wherein $R_1$ may be selected from the group consisting of trityl, benzyl and substituted benzyl wherein substituents on benzyl group may be selected from lower alkyl, lower alkoxy, nitro, halo and amino; R is hydrogen and X is a halogen; followed by
  ii. converting the compound of formula V-II so obtained into a compound of Formula V-II wherein each of R and $R_1$ is hydrogen and X is a halogen; or b)
  i. converting the compound of formula V-II, wherein $R_1$ may be selected from the group consisting of trityl, benzyl and substituted benzyl wherein substituents on benzyl group may be selected from lower alkyl, lower alkoxy, nitro, halo and amino; R may be selected from the groups consisting of benzyl, tosyl, tertiary-butyloxy carbonyl and carbobenzyloxy; and X is a halogen, into a compound of Formula V-II wherein $R_1$ is hydrogen; R may be selected from the groups consisting of benzyl, tosyl, tertiary-butyloxy carbonyl and carbobenzyloxy and X is a halogen, followed by
  ii. converting the compound of formula V-II so obtained into a compound of Formula V-II wherein each of R and R1 is hydrogen; and X is a halogen; or c) converting compound of formula V-II, wherein R₁ may be selected from the group consisting of trityl, benzyl and substituted benzyl wherein substituents on benzyl group may be selected from lower alkyl, lower alkoxy, nitro, halo and amino; R may be selected from the groups consisting of benzyl, tosyl, tertiary-butyloxy carbonyl and carbobenzyloxy; and X is a halogen, directly into a compound of Formula V-II wherein each of R and R₁ is hydrogen and X is a halogen, in a single step.

In one embodiment, deprotection in a) i described above, is performed using a base and deprotection in a) ii, described above, is performed using an acid or by hydrogenation.

Base used in a) i may be an inorganic or organic base as discussed supra.

a) i may be performed in the presence of a suitable solvent. The suitable solvents are as discussed supra.

Acid used in a) ii may be an organic or inorganic acid as discussed supra.

The hydrogenation as described in a) ii may be performed in the presence of a catalyst. The catalysts used for hydrogenation are as discussed supra.

a) ii may be performed in the presence of a suitable solvent. The suitable solvents are as discussed supra.

In one embodiment, deprotection in b) i, described above, is performed using an acid or by hydrogenation and deprotection in a) ii, described above, is performed using an base.

Acid used in b) i may be an organic or inorganic acid as discussed supra.

The hydrogenation as described in b) i may be performed in the presence of a catalyst. The catalysts used for hydrogenation are as discussed supra.

b) i may be performed in the presence of a suitable solvent. The suitable solvents are as discussed supra.

Base used in b) ii may be an inorganic or organic base as discussed supra.

In one embodiment, deprotection in c), described above, may be performed using a base or an acid or by hydrogenation.

In one embodiment, the present invention provides a process for the preparation of a compound of Formula V-II wherein, R₁ may be selected from the group consisting of hydrogen and trityl; R may be selected from the groups consisting of hydrogen and tosyl; and X is chlorine;

V-II the process comprising.

(a) reacting the compound of Formula IV wherein R₁ is trityl;

IV with a compound of Formula III-I wherein X is chlorine; and R is tosyl

III-I to form a compound of formula V-II wherein R₁ is trityl; R is tosyl; and X is chlorine; and

V-II (b) optionally, deprotecting the compound of Formula V-II so obtained to form a compound of Formula V-II wherein at least one of R or R₁ is hydrogen and X is chlorine.

The base used may be an inorganic or organic base. The inorganic base may include an alkali or alkaline earth metal hydroxide, an alkali or alkaline earth metal carbonate and the like, for example sodium hydroxide, potassium hydroxide, sodium carbonate, potassium carbonate and the like. The organic base may include an amine which may be a primary, secondary or a tertiary amine. Examples of organic base include methylamine, ethylamine, triethylamine, propylamine, isopropylamine, diisopropylamine, tertiary butylamine and the like. Preferred inorganic bases include potassium carbonate, sodium carbonate and sodium hydroxide. An organic base may also include pyridine and 1,8-Diazabicyclo[5.4.0]undec-7-ene (DBU). Preferred organic bases include triethylamine and diisopropylamine.

Step (a) as described above, may be performed in the presence of a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methyl pyrrolidone; water; or mixtures thereof. Preferred solvents include an alcohol such as methanol, ethanol and isopropanol; a ketone such as acetone, a nitrile such as acetonitrile; dimethylformamide; dimethylsulfoxide; N-methyl pyrrolidone; and mixtures thereof.

In one embodiment in step (a) described above, reaction of compound of Formula IV wherein $R_1$ is trityl; with a compound of Formula III-I wherein X is chlorine; and R is tosyl, to form a compound of formula V-II wherein $R_1$ is trityl; R is tosyl; and X is chlorine; is performed in the presence of potassium carbonate as base and mixture of dimethylformamide and acetonitrile as solvent.

In one embodiment in step (a) described above, reaction of compound of Formula IV wherein $R_1$ is trityl; with a compound of Formula III-I wherein X is chlorine; and R is tosyl, to form a compound of formula V-II wherein $R_1$ is trityl; R is tosyl; and X is chlorine; is performed in the presence of potassium carbonate as base and dimethylformamide as solvent.

Deprotection in step (b), described above, comprises a)
  i. converting the compound of formula V-II, wherein $R_1$ is trityl; R is tosyl; and X is chlorine; into a compound of Formula V-II wherein $R_1$ is trityl; R is hydrogen; and X is chlorine; followed by
  ii. converting the compound of formula V-II so obtained into a compound of Formula V-II wherein each of R and R1 is hydrogen and X is chlorine; or b)
  i. converting the compound of formula V-II, wherein $R_1$ is trityl; R is tosyl; and X is chlorine into a compound of Formula V-II wherein $R_1$ is hydrogen; R is tosyl; and X is chlorine, followed by
  ii. converting the compound of formula V-II so obtained into a compound of Formula V-II wherein each of R and $R_1$ is hydrogen and X is chlorine; or c) converting compound of formula V-II, wherein $R_1$ is trityl; R is tosyl; and X is chlorine, directly into a compound of Formula V-II wherein each of R and $R_1$ is hydrogen and X is chlorine, in a single step.

In one embodiment, deprotection in a) i, described above, is performed using a base and deprotection in a) ii, described above, is performed using an acid or by hydrogenation.

Base used in a) i may be an inorganic or organic base. The inorganic base may include an alkali or alkaline earth metal hydroxide, an alkali or alkaline earth metal carbonate and the like, for example sodium hydroxide, potassium hydroxide, sodium carbonate, potassium carbonate and the like. The organic base may include an amine which may be a primary, secondary or a tertiary amine. Examples of organic base include methylamine, ethylamine, triethylamine, propylamine, isopropylamine, diisopropylamine, tertiary butylamine and the like. An organic base may also include pyridine and 1,8-Diazabicyclo[5.4.0]undec-7-ene (DBU). Preferred inorganic bases include potassium carbonate, sodium carbonate and sodium hydroxide. Preferred organic bases include triethylamine and diisopropylamine.

a) i as described above may be performed in the presence of a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof. Preferred solvents include an alcohol such as methanol, ethanol and isopropanol; a ketone such as acetone, a haloalkane such as dichloromethane; tetrahydrofuran; water; and mixtures thereof.

In one embodiment, deprotection described in a) i involves conversion of compound of formula V-II, wherein $R_1$ is trityl; R is tosyl; and X is chlorine; into a compound of Formula V-II wherein $R_1$ is trityl; R is hydrogen; and X is chlorine; in presence of sodium hydroxide as base and acetone as solvent.

Acid used in a) ii may be an organic or inorganic acid. The organic acid used may include an acid such as formic acid, acetic acid, citric acid, tartaric acid, bitartaric acid, benzoic acid, lactic acid, malic acid, fumaric acid, succinic acid, gluconic acid, pamoic acid, methanesulfonic acid, benzenesulfonic acid and the like. The inorganic acid used may include an acid such as hydrochloric acid, hydrobromic acid, hydroiodic acid, nitric acid, phosphoric acid, sulfuric acid, trifluoroacetic acid, and the like. Preferred acids include trifluoroacetic acid, hydrochloric acid and hydrobromic acid.

The hydrogenation as described in a) ii may be performed in the presence of a catalyst. The catalyst used may include metal catalysts such as platinum on carbon, palladium on carbon and the like; palladium hydroxide on carbon; platinum hydroxide on carbon; platinum oxide or raney nickel.

a) ii may be performed in the presence of a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof. Preferred solvents include an alcohol such as methanol, ethanol and isopropanol; a ketone such as acetone; an ester such as ethyl acetate; a haloalkane such as dichloromethane; tetrahydrofuran; water; and mixtures thereof.

In one embodiment, deprotection in a) ii described above, involves conversion of compound of Formula V-II wherein $R_1$ is trityl; R is hydrogen; and X is chlorine into compound of formula V-II wherein each of R and $R_1$ is hydrogen and X is chlorine by using trifluoroacetic acid in presence of dichloromethane as solvent.

The compound of formula V-II wherein each of R and $R_1$ is hydrogen and X is chlorine, produced in a) ii, may be purified before further use. The purification may be performed by crystallization from a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof. Preferred solvents include methanol, ethyl acetate, heptane, toluene and mixtures thereof.

In one embodiment, purification may be performed using ethyl acetate.

In one embodiment, purification may be performed using a mixture of ethyl acetate and n-heptane.

In one embodiment, deprotection in b) i, described above, is performed using an acid or by hydrogenation and deprotection in b) ii, described above, is performed using a base.

Acid used in b) i may organic or inorganic acid. The organic acid used may include an acid such as formic acid, acetic acid, citric acid, tartaric acid, bitartaric acid, benzoic acid, lactic acid, malic acid, fumaric acid, succinic acid, gluconic acid, pamoic acid, methanesulfonic acid, benzenesulfonic acid and the like. The inorganic acid used may include an acid such as hydrochloric acid, hydrobromic acid, hydroiodic acid, nitric acid, phosphoric acid, sulfuric acid, trifluoroacetic acid, and the like. Preferred acids include trifluoroacetic acid, hydrochloric acid and acetic acid.

The hydrogenation as described in b) i may be performed in the presence of a catalyst.

The catalysts used are as discussed supra.

b) i may be performed in the presence of a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof. Preferred solvents include an alcohol such as methanol, ethanol and isopropanol; a ketone such as acetone; a haloalkane such as dichloromethane; tetrahydrofuran; water; and mixtures thereof.

In one embodiment, deprotection in b) i, described above, involves conversion of compound of formula V-II, wherein $R_1$ is trityl; R is tosyl; and X is chlorine into a compound of Formula V-II wherein $R_1$ is hydrogen; R is tosyl; and X is chlorine, by using trifluoroacetic acid in presence of dichloromethane as solvent.

Base used in b) ii may be an inorganic or organic base. The inorganic base may include an alkali or alkaline earth metal hydroxide, an alkali or alkaline earth metal carbonate and the like, for example sodium hydroxide, potassium hydroxide, sodium carbonate, potassium carbonate and the like. The organic base may include an amine which may be a primary, secondary or a tertiary amine. Examples of organic base include methylamine, ethylamine, triethylamine, propylamine, isopropylamine, diisopropylamine tertiary butylamine and the like. An organic base may also include pyridine and 1,8-Diazabicyclo[5.4.0]undec-7-ene (DBU). Preferred inorganic bases include potassium carbonate, sodium carbonate and sodium hydroxide. Preferred organic bases include triethylamine and diisopropylamine.

b) ii may be performed in the presence of a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof. Preferred solvents include an alcohol such as methanol, ethanol and isopropanol; a ketone such as acetone; a haloalkane such as dichloromethane; tetrahydrofuran; water; and mixtures thereof.

In one embodiment, deprotection in b) ii, described above, involves conversion of compound of formula V-II $R_1$ is hydrogen; R is tosyl; and X is chlorine, into a compound of Formula V-II wherein each of R and R1 is, hydrogen; by using sodium hydroxide as base and acetone as solvent.

In one embodiment, deprotection in c), described above, may be performed using a base or an acid or by hydrogenation.

In one embodiment, the present invention provides a process for the preparation of a compound of Formula V-II wherein $R_1$ is trityl; R is tosyl; and X is chlorine

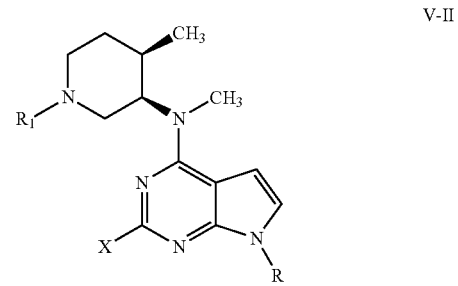

V-II the process comprising (a) reacting the compound of Formula IV wherein $R_1$ is trityl;

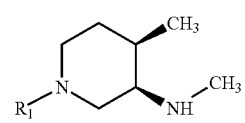

IV with a compound of Formula III-I wherein X is chlorine and R is tosyl;

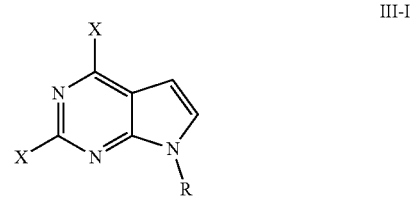

III-I to form a compound of formula V-II wherein $R_1$ is trityl; R is tosyl; and X is chlorine.

Compound of Formula IV wherein $R_1$ is trityl is represented by of Formula XVII in scheme IV.

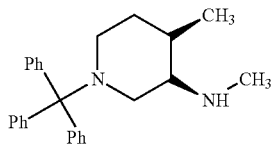

XVII

Step (a) as described above may be performed in the presence of a base. Base used may be may be an inorganic or organic base as discussed supra. Preferred inorganic bases include potassium carbonate, sodium carbonate and sodium hydroxide. Preferred organic bases include triethylamine and diisopropylamine.

Step (a) as described above may be performed in the presence of a suitable solvent. The suitable solvents are as discussed supra.

Preferred solvents include an alcohol such as methanol, ethanol and isopropanol; a ketone such as acetone, a nitrile such as acetonitrile; dimethylformamide; dimethylsulfoxide; N-methylpyrrolidone and mixtures thereof.

In one embodiment, the present invention provides a process for the preparation of a compound of Formula V-II wherein $R_1$ is trityl; R is tosyl; and X is chlorine

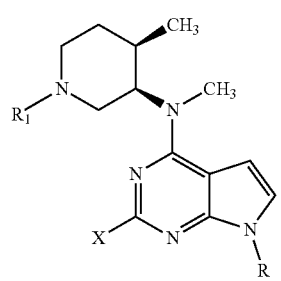

V-II the process comprising
(a) reacting the compound of Formula IV wherein $R_1$ is trityl;

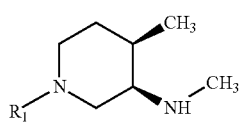

IV with a compound of Formula III-I wherein X is chlorine and R is tosyl;

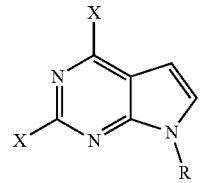

III-I to form a compound of formula V-II wherein $R_1$ is trityl; R is tosyl; and X is chlorine, wherein the reaction is performed in presence of potassium carbonate as base and dimethylformamide as solvent.

In one embodiment, the present invention provides a process for the preparation of a compound of Formula V-II wherein $R_1$ is trityl; R is tosyl; and X is chlorine

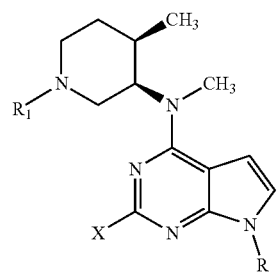

V-II the process comprising
(a) reacting the compound of Formula IV wherein $R_1$ is trityl;

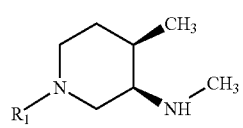

IV with a compound of Formula III-I wherein X is chlorine and R is tosyl;

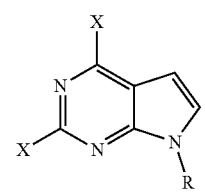

III-I to form a compound of formula V-II wherein $R_1$ is trityl; R is tosyl; and X is chlorine, wherein the reaction is performed in presence of potassium carbonate as base and mixture of dimethylformamide and acetonitrile as solvent.

In one embodiment, the present invention provides a process for the preparation of a compound of Formula V-II wherein $R_1$ is trityl; R is hydrogen; and X is chlorine

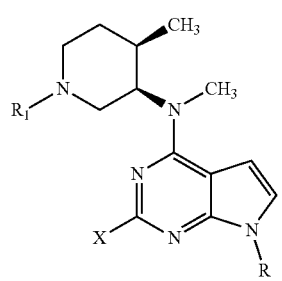

V-II the process comprising
  (a) detosylating the compound of Formula V-II wherein $R_1$ is trityl; R is tosyl; and X is chlorine; to obtain compound of Formula V-II wherein $R_1$ is trityl; R is hydrogen; and X is chlorine Detosylation in Step (a) as described above may be performed in the presence of a base. Base used may be may be an inorganic or organic base as discussed supra. Preferred inorganic bases include potassium carbonate, sodium carbonate and sodium hydroxide. Preferred organic bases include triethylamine and diisopropylamine. In one embodiment the base used is sodium hydroxide.

Detosylation in Step (a) as described above may be performed in the presence of a solvent. The suitable solvents are as discussed supra. Preferred solvents include an alcohol such as methanol, ethanol and isopropanol; a ketone such as acetone, a haloalkane such as dichloromethane; tetrahydrofuran; water; and mixtures thereof.

In one embodiment, detosylation in Step (a) as described above, may be performed in presence of sodium hydroxide as base and acetone as solvent.

In one embodiment, the present invention provides a process for the preparation of a compound of Formula V-II wherein $R_1$ is hydrogen; R is tosyl; and X is chlorine

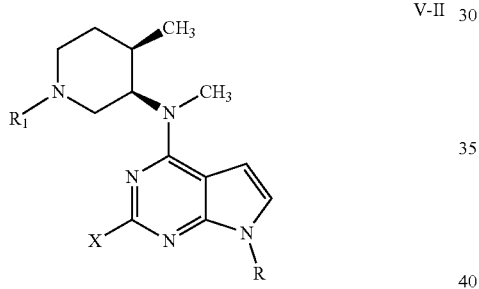

V-II the process comprising
  (a) detritylating the compound of Formula V-II wherein $R_1$ is trityl; R is tosyl; and X is chlorine; to obtain compound of Formula V-II wherein $R_1$ is hydrogen; R is tosyl; and X is chlorine Detritylation in Step (a) as described above may be performed in the presence of an acid. Acid used may organic or inorganic acid as discussed supra. Preferred acids include trifluoroacetic acid, hydrochloric acid and hydrobromic acid.

Detritylation in Step (a) as described above may be performed in the presence of a suitable solvent. The suitable solvents are as discussed supra. Preferred solvents include an alcohol such as methanol, ethanol and isopropanol; a ketone such as acetone; an ester such as ethyl acetate; a haloalkane such as dichloromethane; tetrahydrofuran; water; and mixtures thereof.

In one embodiment, detritylation in Step (a) as described above may be performed in the presence by using trifluoroacetic acid in presence of dichloromethane as solvent.

In one embodiment, the present invention provides a process for preparation of compound of formula V-II wherein each of R and $R_1$ is hydrogen and X is a halogen

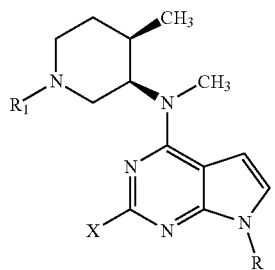

V-II from a compound of Formula V-II wherein $R_1$ is trityl and R is tosyl, the process comprising
  a) sequentially detritylating and detosylating in either order the compound of formula V-II wherein $R_1$ is trityl; R is tosyl and X is a halogen into a compound of formula V-II wherein each of R and $R_1$ is hydrogen and X is a halogen; or
  b) detritylating and detosylating in a single step the compound of formula V-II wherein $R_1$ is trityl; R is tosyl and X is a halogen into a compound of formula V-II wherein each of R and $R_1$ is hydrogen and X is a halogen.

Compound of formula V-II wherein each of R and $R_1$ is hydrogen and X is chlorine is represented by formula VB in scheme 1A

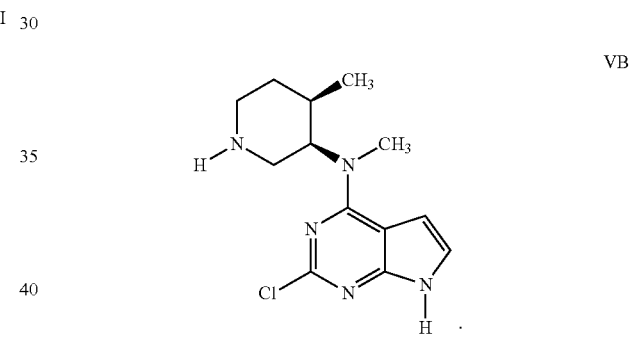

VB

In one embodiment, the present invention provides a process for preparation of compound of formula V-II wherein each of R and $R_1$ is hydrogen and X is chlorine,

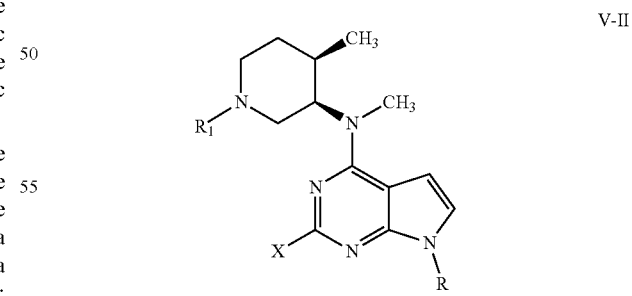

V-II from a compound of Formula V-II wherein $R_1$ is trityl; R is tosyl and X is chlorine the process comprising
  a) sequentially detritylating and detosylating in either order the compound of formula V-II wherein $R_1$ is trityl; R is tosyl and X is chlorine into a compound of formula V-II wherein each of R and $R_1$ is hydrogen and X is chlorine; or b) detritylating and detosylating the compound of formula V-II wherein $R_1$ is trityl; R is tosyl and X is chlorine into a compound of formula V-II wherein each of R and $R_1$ is hydrogen and X is chlorine, in a single step.

In one embodiment in a) above, detritylation of compound of Formula V-II wherein $R_1$ is trityl; R is tosyl and X is chlorine is performed first to form compound of Formula V-II wherein $R_1$ is hydrogen; R is tosyl and X is chlorine, followed by detosylation of compound of Formula V-II wherein $R_1$ is hydrogen; R is tosyl and X is chlorine to form of compound of Formula VB, as depicted in Scheme 1A.

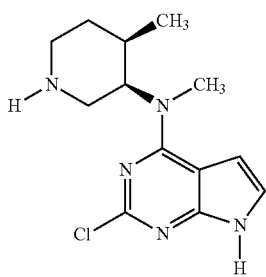

VB

Compound of Formula V-II wherein $R_1$ is hydrogen; R is tosyl and X is chlorine is represented by Formula VA wherein, R is tosyl in scheme 1A

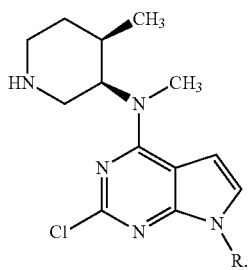

VA

Detritylation of compound of Formula V-II wherein $R_1$ is trityl; R is tosyl and X is chlorine to form compound of Formula V-II wherein $R_1$ is hydrogen; R is tosyl and X is chlorine in a) may be performed by treatment with an acid or by hydrogenation.

The acid used may be an organic or inorganic acid as discussed supra. Preferred acids include trifluoroacetic acid, hydrochloric acid and acetic acid.

The hydrogenation may be performed in the presence of a catalyst. The catalysts used for hydrogenation are as discussed supra.

Detritylation of compound of Formula V-II wherein $R_1$ is trityl; R is tosyl and X is chlorine to form compound of Formula V-II wherein $R_1$ is hydrogen; R is tosyl and X is chlorine, in a) above may be performed in the presence of a suitable solvent. The suitable solvents are as discussed supra. Preferred solvents include an alcohol such as methanol, ethanol and isopropanol; a ketone such as acetone; a haloalkane such as dichloromethane; tetrhaydrofuran; water and mixtures thereof.

In one embodiment, detritylation of compound of Formula V-II wherein $R_1$ is trityl; R is tosyl and X is chlorine to form compound of Formula V-II wherein $R_1$ is hydrogen; R is tosyl and X is chlorine, in a) above may be performed by treatment of compound of Formula V-II with trifluoroacetic acid.

In one embodiment, detritylation of compound of Formula V-II wherein $R_1$ is trityl; R is tosyl and X is chlorine to form compound of Formula V-II wherein $R_1$ is hydrogen; R is tosyl and X is chlorine, in a) above may be performed by treatment of compound of Formula V-II with trifluoroacetic acid in presence of dichloromethane as solvent.

Detosylation of compound of Formula V-II wherein $R_1$ is hydrogen; R is tosyl and X is chlorine to form compound of Formula VB in a) may be performed by treatment of compound of formula V-II wherein $R_1$ is hydrogen; R is tosyl and X is chlorine with a base which may be an inorganic or organic base as discussed supra. Preferred inorganic bases include sodium hydroxide and sodium carbonate. Preferred organic bases include triethylamine and diisopropylamine.

Detosylation of compound of Formula V-II wherein $R_1$ is hydrogen; R is tosyl and X is chlorine to form compound of Formula VB in a) may be carried out in the presence of a suitable solvent. The suitable solvents are as discussed supra. Preferred solvents include alcohols such as methanol, ethanol and isopropanol; ketones such as acetone; a haloalkane such as dichloromethane; tetrahydrofuran; water and mixtures thereof.

In one embodiment, detosylation of compound of Formula V-II wherein R1 is hydrogen; R is tosyl and X is chlorine to form compound of Formula VB in a) may be performed by treatment of compound of Formula V-II wherein R1 is hydrogen; R is tosyl and X is chlorine with sodium hydroxide.

In one embodiment, detosylation of compound of Formula V-II wherein R1 is hydrogen; R is tosyl and X is chlorine to form compound of Formula VB in a) may be performed by treatment of compound of Formula V-II wherein R1 is hydrogen; R is tosyl and X is chlorine with sodium hydroxide as base in the presence of acetone as solvent.

In one embodiment in a) above, detosylation of compound of Formula V-II wherein $R_1$ is trityl; R is tosyl and X is chlorine is performed first, to form compound of Formula V-II wherein $R_1$ is trityl and X is chlorine, followed by detritylation of compound of Formula V-II wherein $R_1$ is trityl and X is chlorine to form of compound of Formula VB, as depicted in Scheme 1A.

Compound of Formula V-II wherein $R_1$ is trityl; R is hydrogen and X is chlorine is represented in scheme 1A by Formula VAA wherein $R_1$ is trityl

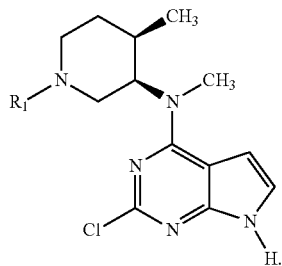

VAA

Detosylation of compound of Formula V-II wherein $R_1$ is trityl; R is tosyl and X is chlorine to form compound of Formula V-II wherein $R_1$ is trityl and X is chlorine, in a) above may be performed by its treatment with a base which may be an inorganic or organic base as discussed supra. Preferred inorganic bases include sodium hydroxide and sodium carbonate. Preferred organic bases include triethylamine and diisopropylamine.

Detosylation of compound of Formula V-II wherein R1 is trityl; R is tosyl and X is chlorine to form compound of Formula V-II wherein R1 is trityl and X is chlorine, in a) may be carried out in the presence of a suitable solvent. The suitable solvents are as discussed supra. Preferred solvents include alcohols such as methanol, ethanol and isopropanol; ketones such as acetone; tetrahydrofuran; halogenated alkanes such as dichloromethane; water and mixtures thereof.

In one embodiment, detosylation of compound of Formula V-II wherein $R_1$ is trityl; R is tosyl and X is chlorine to form compound of Formula V-II wherein $R_1$ is trityl and X is chlorine, in a) above may be performed by a process comprising treatment of compound of Formula V-II with sodium hydroxide.

In one embodiment, detosylation of compound of Formula V-II wherein $R_1$ is trityl; R is tosyl and X is chlorine to form compound of Formula V-II wherein $R_1$ is trityl and X is chlorine, in a) above may be performed by a process by a process comprising treatment of compound of Formula V-II with sodium hydroxide as base in the presence of acetone as solvent.

Detritylation of compound of Formula V-II wherein R is hydrogen; $R_1$ is trityl and X is chlorine in a) may be performed by treatment with an acid or by hydrogenation.

The acid used may be an organic or inorganic acid as discussed supra. Preferred acids include trifluoroacetic acid, hydrochloric acid, hydrobromic acid and acetic acid.

The hydrogenation may be performed in the presence of a catalyst. The catalysts used for hydrogenation are as discussed supra.

Detritylation of compound of Formula V-II wherein R is hydrogen; $R_1$ is trityl and X is chlorine in a) to form compound of Formula VB may be performed in the presence of a suitable solvent. The suitable solvents are as discussed supra. Preferred solvents include an alcohol such as methanol, ethanol and isopropanol; a ketone such as acetone; esters such as ethyl acetate; a haloalkane such as dichloromethane; tetrahydrofuran; water and mixtures thereof.

In one embodiment, detritylation of compound of Formula V-II wherein R is hydrogen; R1 is trityl and X is chlorine to form compound of Formula VB may be performed by treatment of compound of Formula V-II wherein R is hydrogen; R1 is trityl and X is chlorine with trifluoroacetic acid.

In one embodiment, detritylation of compound of Formula V-II wherein R is hydrogen; R1 is trityl and X is chlorine to form compound of Formula VB may be performed by treatment of compound of Formula V-II wherein R is hydrogen; R1 is trityl and X is chlorine with trifluoroacetic acid in presence of dichloromethane as solvent.

Detritylating and detosylating in a single step, the compound of formula V-II wherein $R_1$ is trityl; R is tosyl and X is chlorine into a compound of formula V-II wherein each of R and $R_1$ is hydrogen and X is chlorine, in a single step may be performed by treatment of compound of formula V-II wherein $R_1$ is trityl; R is tosyl and X is chlorine, with an acid or a base or by hydrogenation.

The compound of formula V-II wherein each of R and $R_1$ is hydrogen and X is chlorine is represented by Formula VB

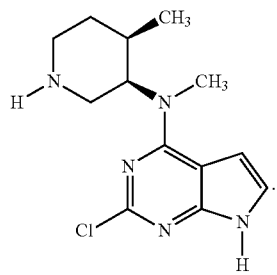

The compound of formula V-II wherein each of R and $R_1$ is hydrogen and X is chlorine, produced in a) ii, may be purified before further use. The purification for VB is as discussed before.

In one embodiment, the present invention provides a process comprising dehalogenation of compound of Formula V-II wherein each of R and $R_1$ is hydrogen; X is a halogen to form a compound of Formula XII followed by conversion of compound of Formula XII into tofacitinib.

In one embodiment, the present invention provides a process comprising dechlorination of compound of Formula V-II wherein each of R and $R_1$ is hydrogen; and X is chlorine to form a compound of Formula XII followed by conversion of compound of Formula XII into tofacitinib.

In one embodiment, the present invention provides a process for preparation of compound of XII, depicted in schemes 1 and 1A, by a process of dehalogenation of compound of formula V-II, wherein each of R and $R_1$ is hydrogen and X is halogen

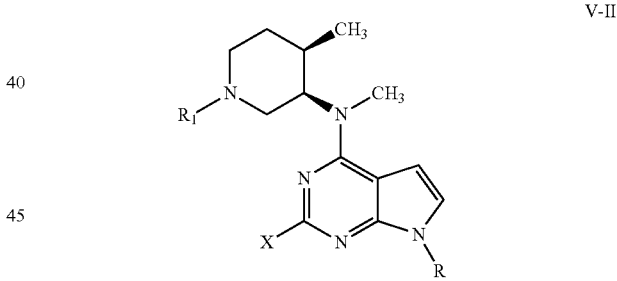

In one embodiment, the present invention provides a process for preparation of compound of XII, depicted in schemes 1 and 1A, by a process of dechlorination of compound of formula V-II, represented by formula VB in schemes 1 and 1A,

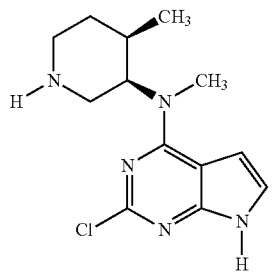

VB wherein each of R and $R_1$ is hydrogen and X is halogen

Dechlorination of compound of Formula VB may be performed by hydrogenation of compound of formula VB. The hydrogenation may be performed in the presence of a catalyst. The catalyst used may include metal catalysts such as platinum on carbon, palladium on carbon and the like; palladium hydroxide on carbon; platinum hydroxide on carbon; platinum oxide or raney nickel.

The reaction may be performed in the presence of a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof. Preferred solvents include alcohols such as methanol, ethanol and isopropanol; and ethers such as isopropyl ether, methyl tert-butyl ether.

The reaction may be performed under acidic conditions or basic conditions.

Acidic conditions may be provided by using an acid during hydrogenation. The acid used may be an organic or inorganic acid as discussed supra. Preferred acids include acetic acid, hydrochloric acid and the like.

Basic conditions may be provided by using a base during hydrogenation. The base used may be an organic or inorganic base as discussed supra. Preferred inorganic bases include sodium carbonate, potassium carbonate and the like. Preferred organic bases include 1,8-Diazabicyclo[5.4.0]undec-7-ene (DBU), triethylamine, diisopropylamine and the like.

In one embodiment, the present invention provides a process for preparation of compound of Formula XII by a process comprising hydrogenation of compound of Formula VB.

In one embodiment, the hydrogenation compound of Formula VB may be carried out in acidic medium.

In one embodiment, the hydrogenation compound of Formula VB may be carried out in basic medium.

In one embodiment, the present invention provides a process for preparation of compound of Formula XII wherein, hydrogenation of compound of Formula VB is performed using palladium hydroxide on carbon as catalyst in the presence of a mixture of ethanol and acetic acid.

In one embodiment, the present invention provides a process for preparation of compound of Formula XII wherein, hydrogenation of compound of Formula VB is performed using palladium on carbon as catalyst in the presence of methanol as solvent.

In one embodiment, the present invention provides a process for preparation of compound of Formula XII wherein, hydrogenation of compound of Formula VB is performed using palladium hydroxide on carbon as catalyst in the presence of methanol as solvent.

In one embodiment, the present invention provides a provides a process for preparation of compound of Formula XII wherein, hydrogenation of compound of Formula VB is performed using palladium on carbon as catalyst in the presence of methanol as solvent and Diazabicyclo[5.4.0]undec-7-ene (DBU) as base.

In one embodiment, the present invention provides a provides a process for preparation of compound of Formula XII wherein, hydrogenation of compound of Formula VB is performed using palladium hydroxide on carbon as catalyst in the presence of methanol as solvent and Diazabicyclo [5.4.0]undec-7-ene (DBU) as base.

As depicted in schemes 1 and 1A, the compound of Formula XII may be converted into tofacitinib, a compound of Formula I, by treating the compound of Formula XII with cyanoacetic acid or derivatives thereof. The cyanoacetic acid derivatives used may be ester derivatives, acid halides, or amide derivatives.

In one embodiment, the present invention provides a process for preparation of tofacitinib or salts thereof, by a process comprising treatment of compound of Formula XII with cyanoacetic acid or derivatives thereof.

The reaction may be performed in the presence of a base which may be an organic or inorganic base. The inorganic base may include an alkali or alkaline earth metal hydroxide, an alkali or alkaline earth metal carbonate and the like. Examples of inorganic base include sodium hydroxide, potassium hydroxide, sodium carbonate, potassium carbonate and the like. The organic base may, include an amine which may be a primary, secondary or tertiary amine. Examples of organic base include methylamine, ethylamine, triethylamine, propylamine, isopropylamine, diisopropylamine, tertiary butylamine. Organic base may also include pyridine, N-methylmorpholine and 1,8-Diazabicyclo[5.4.0]undec-7-ene can be used. Preferred bases include N-methylmorpholine, 1,8-Diazabicyclo[5.4.0]undec-7-ene, pyridine, diisopropylamine and triethyamine.

The reaction may be performed in the presence of a suitable solvent. The suitable solvents are as discussed supra. Preferred solvents include alcohols such as methanol, ethanol, isopropanol, n-propanol, butanol; haloalalkanes such as dichloromethane; aromatic hydrocarbons such as toluene; tetrahydrofuran; dimethyl formamide; and mixtures thereof.

The reaction may be performed in the presence of a coupling agent. Coupling agents which may be used include methylchloroformate, ethylchloroformate, isobutylchloroformate, N,N'-Dicyclohexylcarbodiimide, 1-ethyl-3-(3-dimethylaminopropyl)carbodiimide or N-Hydroxybenzotriazole. Preferred coupling agents include isobutylchloroformate and ethylchloroformate.

In one embodiment, the present invention provides a process for preparation of tofacitinib or salts thereof, by a process comprising treatment of compound of Formula XII with cyanoacetic acid.

In one embodiment, the present invention provides a process for preparation of tofacitinib or salts thereof, by a process comprising treatment of compound of Formula XII with cyanoacetic acid in presence of a coupling agent.

In one embodiment, the present invention provides a process for preparation of tofacitinib or salts thereof wherein, compound Formula XII is treated with cyanoacetic acid in presence of dichloromethane as solvent, N-methylmorpholine as base and isobutylchloroformate as coupling agent.

In one embodiment, the present invention provides a process for preparation of tofacitinib wherein, compound Formula XII is treated with cyanoacetyl chloride.

In one embodiment, the present invention provides a process for preparation of tofacitinib wherein, compound Formula XII is treated with cyanoacetyl chloride in dichloromethane.

In one embodiment, the present invention provides a process for preparation of tofacitinib wherein, compound Formula XII is treated with ester derivatives of cyanoacetic acid. Examples of ester derivatives of cyanoacetic acid include methyl cyanoacetate, ethyl cyanoacetate, n-propyl cyanoacetate, tert-butyl cyanoacetate and the like.

In one embodiment, the present invention provides a process for preparation of tofacitinib wherein, compound Formula XII is treated with methylcyanoacetate in presence of 1,8-Diazabicyclo[5.4.0]undec-7-ene as base.

In one embodiment, the present invention provides a process for preparation of tofacitinib wherein, compound Formula XII is treated with methylcyanoacetate in presence of 1,8-Diazabicyclo[5.4.0]undec-7-ene as base and ethanol as solvent.

In one embodiment, the present invention provides a process for preparation of tofacitinib wherein, compound Formula XII is treated with methylcyanoacetate in presence of 1,8-Diazabicyclo[5.4.0]undec-7-ene as base and tetrahydrofuran as solvent.

In one embodiment, the present invention provides a process for preparation of compound of Formula IV, wherein $R_1$ is trityl, comprising a process as depicted in scheme 4.

thereof; wherein $R_1$ may be selected from the group consisting of trityl, 4-methoxybenzyl and 3,4-dimethoxybenzyl comprising

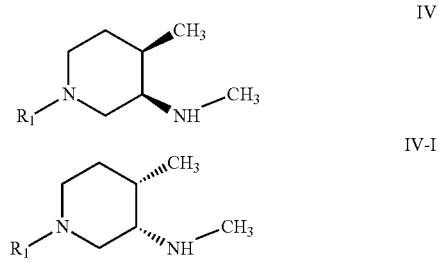

(a) converting a compound of Formula XIV to a compound of formula XV-I wherein $R_1$ may be selected from the group consisting of trityl, 4-methoxybenzyl and 3,4-dimethoxybenzyl; and $R_3$ is selected from the group consisting of C1-5 straight or branched chain alkyl;

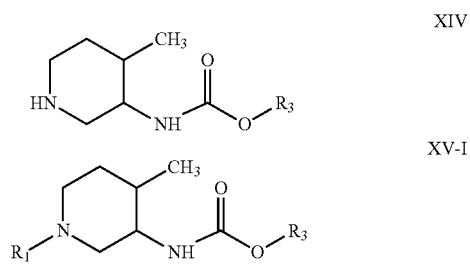

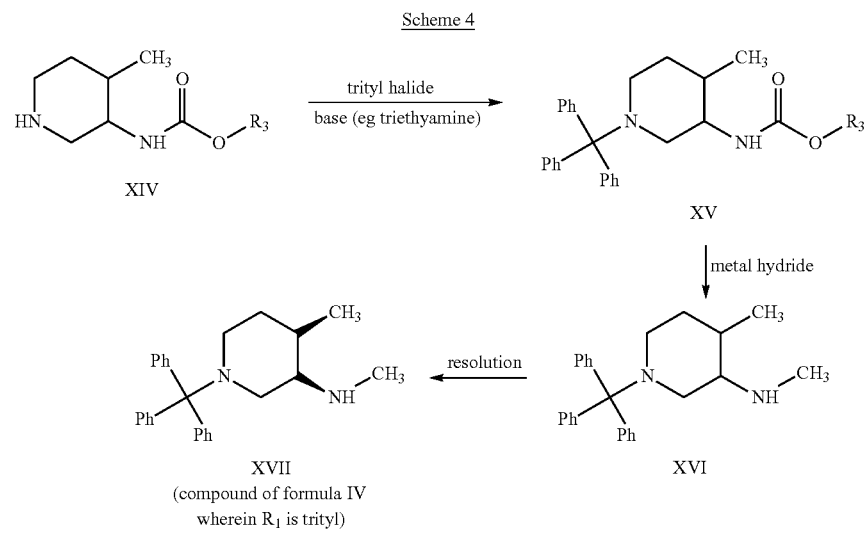

$R_3$, as depicted in scheme 4, is selected from the group consisting of C1-5 straight or branched chain alkyl, for example methyl, ethyl, n-propyl, isopropyl, n-butyl and the like.

The present invention provides a process for the preparation of a either compound of Formula IV or IV-I and salts (b) converting the compound of Formula XV-I so obtained to a compound of Formula XVI-I; followed by

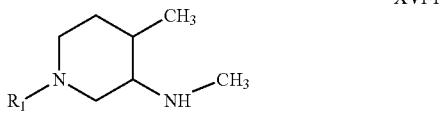

(c) resolution of compound of Formula XVI-I so obtained.

Step (a), described above, may be performed in presence of a base as discussed supra.

Step (a), described above, may be performed in presence of a may be performed in the presence of a suitable solvent. The suitable solvents are as discussed supra.

In step (b) described above, compound of Formula XV-I wherein $R_3$ is as defined above, may be converted into compound of formula XVI-I or its salt by a process comprising reduction of compound of Formula XV-I. The reduction may be performed using a suitable hydride. The suitable hydride may include metal hydrides such as sodium borohydride, potassium borohydride, lithium borohydride, lithium laiuminium hydride, vitride and the like; borane and diborane.

Step (b) for conversion of compound of formula XV-I wherein $R_3$ is as defined above to compound of Formula XVI-I, as described above, may be performed in presence of a suitable solvent. The suitable solvents are as discussed supra. Preferred solvents may include an alcohol such as methanol, ethanol, 1-propanol, 2-propanol, 1-butanol, 2-butanol, 1-pentanol, 1-octanol and the like; an ester such as methyl acetate, ethyl acetate, n-propyl acetate, tert-butyl acetate and the like; a haloalkane such as dichloromethane, chloroform and the like; an aromatic hydrocarbon such as toluene; dimethyl formamide; and tetrahydrofuran.

In step (c) as described above, compound of formula XVI-I may be resolved to form a compound of formula IV or IV-I wherein $R_1$ may be selected from the group consisting of trityl, 4-methoxybenzyl and 3,4-dimethoxybenzyl.

In step (c) as described above, resolution of compound of Formula XVI-I, wherein Rd may be selected from the group consisting of trityl, 4-methoxybenzyl and 3,4-dimethoxybenzyl, may be performed using a resolving agent to prepare a compound of Formula IV or IV-I. The resolving agent used may be, for example, Di-p-toluyl-L-tartaric acid, Dibenzoyl-L-tartaric acid, L-tartaric acid, Di-p-toluyl-D-tartaric acid, Dibenzoyl-D-tartaric acid, D-tartaric acid and the like.

In one embodiment, resolution in step (c) is performed by a process comprising resolution of a compound of formula XVI-I wherein $R_1$ may be selected from the group consisting of trityl, 4-methoxybenzyl and 3,4-dimethoxybenzyl using Di-p-toluyl-L-tartaric acid as a resolving agent.

In one embodiment, resolution in step (c) is performed by a process comprising resolution of a compound of formula XVI-I wherein $R_1$ may be selected from the group consisting of trityl, 4-methoxybenzyl and 3,4-dimethoxybenzyl using Di-p-toluyl-D-tartaric acid as a resolving agent.

The resolution of compound of Formula XVI-I may be performed in a suitable solvent. The suitable solvents are discussed supra. Preferred solvents include an alcohol such as methanol, ethanol, 1-propanol, 2-propanol, 1-butanol, 2-butanol, 1-pentanol, 1-octanol and the like; an ester such as ethyl acetate, n-propyl acetate, tert-butyl acetate and the like; a ketone such as acetone, propanone, methylisobutylketone and the like; water or mixtures thereof.

In one embodiment, resolution in step (c) may be performed using Di-p-toluyl-L-tartaric acid as a resolving agent in presence of acetone as solvent.

In one embodiment, resolution in step (c) may be performed using Di-p-toluyl-D-tartaric acid as a resolving agent in presence of aqueous methanol as solvent.

The diastereomeric salt so prepared (Di-p-toluyl-L-tartaric acid salt of IV-I or Di-p-toluyl-D-tartaric acid salt of compound of formula IV) may be purified by recrystallization from a suitable solvent. The suitable solvents are discussed supra. The preferred solvent may include an alcohol such as methanol, ethanol, 1-propanol, 2-propanol, 1-butanol, 2-butanol, 1-pentanol, 1-octanol and the like; a ketone such as acetone, propanone and the like; water; or mixtures thereof.

In one embodiment, the present invention provides a process for the purification of Di-p-toluyl-L-tartaric acid salt of compound of IV-I using a mixture of ethanol and water.

In one embodiment, the present invention provides a process for the purification of Di-p-toluyl-D-tartaric acid salt of compound of Formula IV using a mixture of methanol and water.

The Di-p-toluyl-L-tartaric acid salt of IV-I or Di-p-toluyl-D-tartaric acid salt of compound of Formula IV may be converted to compound of Formula IV-I or IV respectively before further reaction or treatment, by treatment with a base. The base used may be an organic or inorganic base. The inorganic bases include alkali or alkaline earth metal hydroxides, alkali or alkaline earth metal carbonates and the like, for example sodium hydroxide, potassium hydroxide, sodium carbonate, potassium carbonate and the like. The organic base may be an amine which may be a primary, secondary or tertiary amine. Examples of organic base include methylamine, ethylamine, triethylamine, propylamine, isopropylamine, diisopropylamine, tertiary butylamine and the like. Organic base also includes pyridine and DBU.

Optionally, the compound of Formula IV or IV-I may be purified by recrystallization using an alcohol and water mixture. The alcohol may be an aliphatic straight or branched chain alcohol like methanol, ethanol, n-propanol, isopropanol and the like.

The diastereomeric salt of compound of Formula IV or IV-I may optionally be converted into an acid addition salt. Acid addition salts may be organic or inorganic acid addition salts. The various organic and inorganic acid addition salts may be hemi, mono or diacid addition salts. The organic acid addition salts include mono and diacid addition salts of acids such as formic acid, oxalic acid, acetic acid, citric acid, tartaric acid, benzoic acid, lactic acid, malic acid, fumaric acid, succinic acid, gluconic acid, pamoic acid, methanesulfonic acid, benzenesulfonic acid and the like. The inorganic acid addition salts include mono and diacid addition salts of acids such as hydrochloric acid, hydrobromic acid, hydroiodic acid, nitric acid, phosphoric acid, sulfuric acid and the like, before further reaction.

In one embodiment the present invention provides a process for the preparation of a compound of Formula IV and salts thereof; wherein $R_1$ may be selected from the group consisting of trityl, 4-methoxybenzyl and 3,4-dimethoxybenzyl

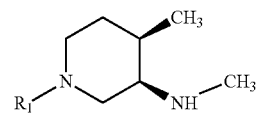

IV comprising (a) converting a compound of Formula XIV to a compound of formula XV-I wherein $R_1$ may be selected from the group consisting of trityl, 4-methoxybenzyl and 3,4-dimethoxybenzyl

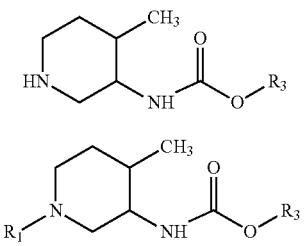
XIV

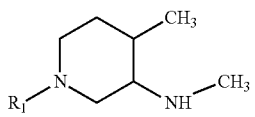
XV-I (b) converting the compound of Formula XV-I so obtained to a compound of Formula XVI-I; followed by

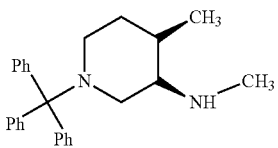
XVI-I (c) resolution of compound of Formula XVI-I so obtained.

Compound of Formula IV wherein $R_1$ is trityl is represented by Formula XVII in scheme IV.

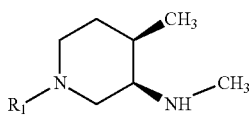
XVII

In one embodiment, the present invention provides a process for the preparation of a compound of Formula IV and salts thereof; wherein $R_1$ is trityl

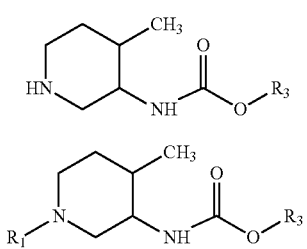
IV comprising
(a) converting a compound of Formula XIV to a compound of formula XV-I wherein $R_1$ is trityl; and $R_3$ is selected from the group consisting of C1-5 straight or branched chain alkyl, preferably methyl;

XIV

XV-I (b) converting the compound of Formula XV so obtained to a compound of Formula XVI-I wherein R1 is trityl and $R_3$ is selected from the group consisting of C1-5 straight or branched chain alkyl, preferably methyl; followed by

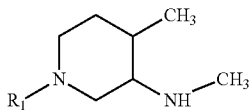
XVI-I (c) resolution of compound of Formula XVI-I so obtained.

Compound of Formula XV-I wherein $R_1$ is trityl is represented by formula XV in scheme 4.

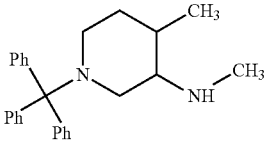
XV

Compound of Formula XVI-I wherein R1 is trityl is represented by compound of formula XVI in scheme 4

XVI

In step (a) described above, compound of Formula XIV may be converted into compound of formula XV by a process comprising tritylation of compound of Formula XIV, wherein for compounds of Formula XIV and XV $R_3$ is as defined above. Tritylation may be done using a trityl halide which may be trityl chloride.

Step (a), described above, may be performed in presence of a base. Base used may be an inorganic or organic base as discussed supra. Preferred inorganic bases include potassium carbonate, sodium carbonate and sodium hydroxide. Preferred organic bases include methylamine, triethylamine and diisopropylamine.

Step (a), described above, may be performed in presence of a suitable solvent. The suitable solvents are as discussed supra. Preferred solvents include nitriles such as acetonitrile, esters such as ethyl acetate and ketones such as acetone.

In one embodiment, in step (a) described above, compound of Formula XIV may be converted into compound of formula XV by a process comprising tritylation of compound of Formula XIV, wherein for compounds of Formula XIV and XV $R_3$ is methyl with trityl chloride in presence of triethylamine as base and acetonitrile as solvent.

In step (b) described above, compound of Formula XV wherein $R_3$ is as defined above, may be converted into compound of formula XVI or its salt by a process comprising reduction of compound of Formula XV. The reduction may be carried out using a suitable hydride. The suitable hydride may include metal hydrides such as sodium borohydride, potassium borohydride, lithium borohydride, lithium aluminum hydride, vitride (also known as sodium bis(2-methoxyethoxy)aluminumhydride) and the like; borane and diborane.

In one embodiment, reduction may be carried out using lithium aluminium hydride.

In one embodiment, reduction may be carried out using vitride.

In one embodiment, reduction of compound of Formula XV wherein $R_3$ is methyl may be carried out using lithium aluminium hydride.

In one embodiment, reduction of compound of Formula XV wherein $R_3$ is methyl may be carried out using vitride.

Step (b) may be performed in presence of a suitable solvent. The suitable solvents are as discussed supra. Preferred solvents include toluene and tetrahydrofuran In one embodiment, in step (b) described above conversion of compound of Formula XV wherein $R_3$ is methyl, to compound of formula XVI or salt thereof may be performed by a process comprising reduction of compound of Formula XV with lithium aluminium hydride in presence of tethaydrofuran as solvent.

Compound of Formula XVI may be isolated as oil or as a solid. Compound of Formula XVI isolated as oil may be further crystallized to get a solid. The crystallization may be performed using a suitable solvent. The suitable solvents are discussed supra. The preferred solvent may include an alcohol such as methanol, ethanol, 1-propanol, 2-propanol, 1-butanol, 2-butanol, 1-pentanol, 1-octanol and the like; hydrocarbons such as hexane, heptanes and the like.

In one embodiment, the present invention provides a process wherein compound of Formula XVI isolated as oil may be crystallized from methanol.

In step (c) as described above, compound of formula XVI may be resolved to form a compound of formula IV wherein $R_1$ is trityl which is represented by formula XVII in scheme 4.

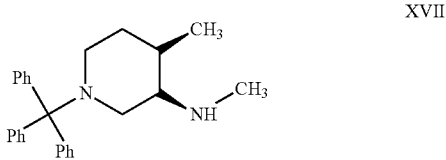

XVII

In step (c) as described above, resolution of compound of Formula XVI may be performed using a resolving agent to prepare a compound of Formula XVII. The resolving agent used may be, for example, Di-p-toluyl-D-tartaric acid, Dibenzoyl-D-tartaric acid, D-tartaric acid and the like.

In one embodiment, resolution in step (c) is performed by a process comprising resolution of a compound of formula XVI using Di-p-toluyl-D-tartaric acid as a resolving agent.

The resolution of compound of Formula XVI may be performed in a suitable solvent. The suitable solvents are as discussed supra. Preferred solvents include alcohols such as methanol, ethanol, isopropanol and the like; ketones such as acetone and the like; esters such as ethylacetate and the like; water; and mixtures thereof.

In one embodiment, resolution in step (c) may be performed by a process comprising resolution of a compound of formula XVI using Di-p-toluyl-D-tartaric acid as a resolving agent in presence of aqueous methanol as solvent.

The diastereomeric salt so prepared (Di-p-toluyl-D-tartaric acid salt of compound of formula XVII) may be purified by recrystallization from a suitable solvent. The suitable solvents are as discussed supra. The preferred solvent include an alcohol such as methanol, ethanol, 1-propanol, 2-propanol, 1-butanol, 2-butanol, 1-pentanol, 1-octanol and the like; a ketone such as acetone, propanone and the like; water; or mixtures thereof.

In one embodiment, the present invention provides a process for the purification of Di-p-toluyl-D-tartaric acid salt of compound of Formula XVII using a mixture of methanol and water.

In one embodiment, the present invention provides Di-p-toluyl-D-tartaric acid salt of compound of Formula XVII in a chiral purity of at least 99.5%.

The Di-p-toluyl-D-tartaric acid salt of compound of Formula XVII may be converted to XVII, before further reaction or treatment, by treatment with a base. The base used may be an organic or inorganic base. The inorganic bases include alkali or alkaline earth metal hydroxides, alkali or alkaline earth metal carbonates and the like, for example sodium hydroxide, potassium hydroxide, sodium carbonate, potassium carbonate and the like. The organic base may be an amine which may be a primary, secondary or tertiary amine. Examples of organic base include methylamine, ethylamine, triethylamine, propylamine, isopropylamine, tertiary butylamine and the like. Organic base also includes pyridine and DBU.

In one embodiment, the present invention provides a process for conversion of the Di-p-toluyl-D-tartaric acid salt of compound of Formula XVII to compound of Formula XVII using potassium carbonate as base. The compound of Formula XVII may be extracted into an organic solvent. The suitable solvents are as discussed supra. The preferred solvent include an ester such as ethyl acetate, propyl acetate, butyl actetate and the like; a haloalkane such as dichloromethane, chloroform and the like; aromatic hydrocarbons such as toluene and the like. Preferred solvents include haloalkanes such as dichloromethane; and esters such as ethyl acetate and aromatic hydrocarbons such as toluene. The solvent may be removed to afford a residue containing compound of Formula XVII. The compound of Formula XVII so produced may be crystallized in suitable solvent. The suitable solvents are as discussed supra. The preferred solvent may include an alcohol such as methanol, ethanol, 1-propanol, 2-propanol, 1-butanol, 2-butanol, 1-pentanol, 1-octanol and the like; an ester such as methyl acetate, ethyl acetate, n-propyl acetate, tert-butyl acetate and the like; a hydrocarbon such as n-hexane, n-heptane and the like. Preferred solvents for crystallization include alcohols such as methanol, ethanol; hydrocarbons such as n-hexane; and esters such as ethylacetate.

The compound of Formula XVI may be purified before the resolution step. The purification step may involve conversion of compound of Formula XVI to an acid addition salt thereof. The acid addition salt may include organic acid addition salts and inorganic acid addition salts. The various organic and inorganic acid addition salts may be hemi, mono or diacid addition salts. The organic acid addition salts include mono and diacid addition salts of acids such as formic acid, oxalic acid, acetic acid, citric acid, tartaric acid, benzoic acid, lactic acid, malic acid, fumaric acid, succinic acid; gluconic acid, pamoic acid, methanesulfonic acid, benzenesulfonic acid and the like. The inorganic acid addition salts include mono and diacid addition salts of acids such as hydrochloric acid, hydrobromic acid, hydroiodic acid, nitric acid, phosphoric acid, sulfuric acid and the like.

The conversion of compound of Formula XVI to its acid addition salt may be performed in the presence of a suitable solvent. The suitable solvents are as discussed supra. The preferred solvent includes an ester such as ethyl acetate, n-propyl acetate, tert-butyl acetate and the like; a ketone solvent such as acetone, propanone, methylisobutylketone and the like.

The acid addition salt of compound of Formula XVI may be hydrochloride or dihydrochloride salt. The hydrochloride or dihydrochloride salt may be prepared by treatment of compound of Formula XVI with hydrogen chloride gas, ethylacetate hydrochloride, isopropanolic hydrochloride, ethanolic hydrochloride, methanolic hydrochloride or diisopropylether hydrochloride.

In one embodiment, the present invention provides a process for conversion of hydrochloride or dihydrochloride salt of compound of Formula XVI by process comprising treatment of compound of Formula XVI with ethyl acetate hydrochloride in ethylacetate as solvent.

In one embodiment, the present invention provides a process for conversion of compound of formula IV, wherein $R_1$ may be selected from the group consisting of trityl, 4-methoxybenzyl and 3,4-dimethoxybenzyl into tofacitinib or salts thereof.

In one embodiment, the present invention provides a process for conversion of compound of formula IV, wherein $R_1$ is trityl into tofacitinib or salts thereof.

In one embodiment, the present invention provides use of
a. a compound of Formula IVA

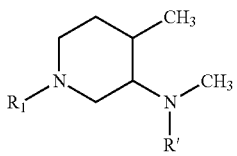

IVA wherein, $R_1$ may be selected from the group consisting of hydrogen and trityl; R' may be hydrogen or a group represented by Formula Y

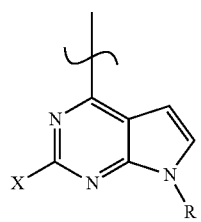

Y wherein X is a halogen and R may be selected from the groups consisting of hydrogen and tosyl; with the proviso that both $R_1$ and R' can not be hydrogen at the same time; or
b. a compound of Formula V-I wherein $R_1$ may be hydrogen or trityl; R may be hydrogen or tosyl and X is a halogen; or

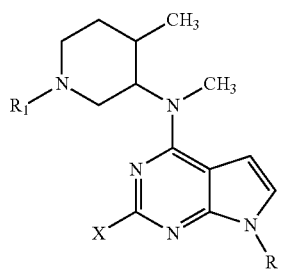

V-I c. a compound of Formula V wherein $R_1$ may be hydrogen or trityl and R may be hydrogen or tosyl; or

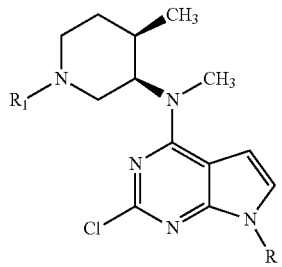

V d. a compound of Formula IV wherein $R_1$ is trityl

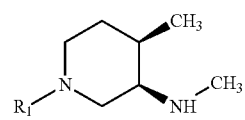

IV for the preparation of tofacitinib or salts thereof.

Tofacitinib, a compound of Formula I may be converted into various acid addition salts of various organic or inorganic acids. The organic and inorganic acid addition salts of tofacitinib may be hemiacid addition salts or monoacid addition salt or diacid addition salts. The organic acid addition salts include hemi, mono and diacid addition salts of acids such as formic acid, oxalic acetic acid, citric acid, tartaric acid, benzoic acid, lactic acid, malic acid, fumaric acid, succinic acid, gluconic acid, pamoic acid, methanesulfonic acid, benzenesulfonic acid and the like. The inorganic acid addition salts include mono and diacid addition salts of acids such as hydrochloric acid, hydrobromic acid, hydroiodic acid, nitric acid, phosphoric acid, sulfuric acid and the like.

The preparation of acid addition salt of tofacitinib (for example mono citrate salt) may be performed in the presence of a suitable solvent. The suitable solvents are as discussed supra.

Preferred solvents include ketones such as acetone; alcohols such as ethanol and isopropanol; and ethers such as diisopropyl ether and methyl tert-butyl ether.

Tofacitinib may be isolated as oil or as a solid. Tofacitinib isolated as oil may be recrystallized using a suitable solvent to obtain tofacitinib in solid form. Suitable solvents are as discussed supra. Preferable solvents include alcoholic solvents; esters like ethyl actetate; halogenated hydrocarbons like methylene dichloride; and dioxane.

In one embodiment, the present invention provides preparation of tofacitinib in the form of a solid by a process comprising recrystallizing or slurrying or triturating tofacitinib in an alcoholic solvent. Examples of alcoholic solvents used include methanol, ethanol, n-propanol, isopropanol, butanol, isobutanol and the like.

In one embodiment, the present invention provides preparation of tofacitinib in the form of a solid by a process comprising triturating tofacitinib in methanol or n-propanol.

In one embodiment, the present invention provides preparation of tofacitinib monocitrate by a process comprising treatment of tofacitinib with citric acid in a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; and mixtures thereof.

In one embodiment the solvent is acetone.

In one embodiment, the present invention provides a process for purification of tofocitinib monocitrate by a process comprising recrystallization form a suitable solvent. The suitable solvent may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof. Preferably, the suitable solvent may be methanol, ethanol, n-propanol, isopropanol, acetonitrile, dimethylformamide, dimethylsulfoxide, dioxane, water and mixtures thereof.

In one embodiment, the present invention provides a process for purification of tofocitinib monocitrate by a process comprising recrystallization from a mixture of acetonitrile and water.

In one embodiment, the present invention provides a process for purification of tofocitinib monocitrate by a process comprising recrystallization from a mixture of dimethylformamide and water.

In one embodiment, the present invention provides a process for purification of tofocitinib monocitrate by a process comprising recrystallization from a mixture of methanol and water.

In one embodiment, the present invention provides tofocitinib monocitrate substantially free of any one or more of the following compounds of formula A, B, and C

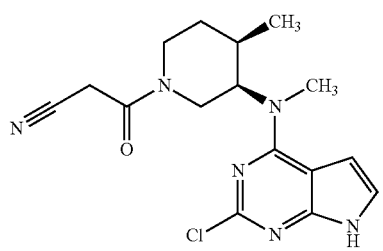

A

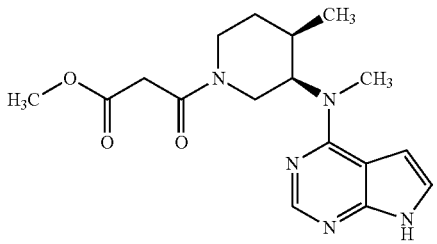

B

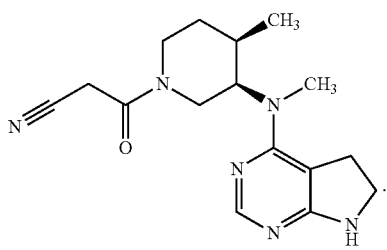

C

In one embodiment, the present invention provides tofacitinib hemicitrate substantially free of any one or more of the following compounds of formula A, B, and C

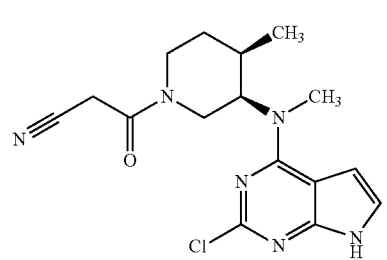

A

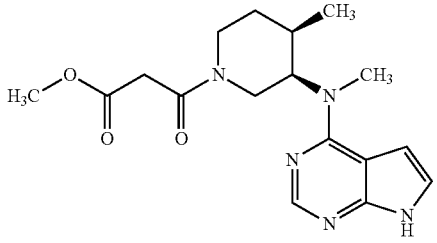

B

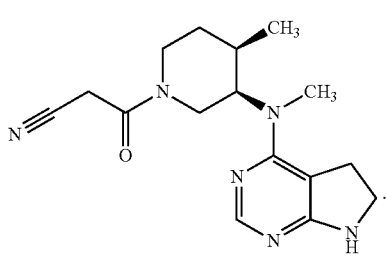

C

The term "substantially free" means the compounds of formula A, B and C are each present to an extent of less than 0.15% relative to the amount of tofacitinib, preferably less than 0.1%, more preferably absent.

In one embodiment, the present invention provides a process for preparation of tofacitinib hemicitrate by a process comprising reacting 1 mole of tofacitinib with 0.5 mole of citric acid in a suitable solvent.

In one embodiment, the present invention provides a process for preparation of tofacitinib hemicitrate by a process comprising treating 1 mole of tofacitinib with 0.5 mole of citric acid in a suitable solvent at a temperature of more than 55° C.

In one embodiment, the present invention provides a process for preparation of tofacitinib hemicitrate by a process comprising treating 1 mole of tofacitinib with 0.5 mole of citric acid in a suitable solvent at a temperature range of 65-250° C., preferably 60-150° C.

Suitable solvent for preparation of tofacitinib hemicitrate may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof.

In one embodiment, the suitable solvent is ethanol.

In one embodiment, the suitable solvent is mixture of methanol and water.

In one embodiment, the present invention provides a process for purification of tofacitinib hemi citrate by a process comprising recrystallization form an organic solvent. may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof.

Tofacitinib may be converted into its monoxalate salt.

The present invention provides a novel monoxalate salt of tofacitinib.

Tofacitinib monoxalate may be prepared by treatment of tofacitinib with oxalic acid.

The reaction may be performed in the presence of a suitable solvent. The suitable solvent may include, alcohols such as methanol, ethanol, 1-propanol, isopropanol, 1-butanol, 2-butanol, 1-pentanol, 1-octanol and the like; ketones such as acetone, propanone, methylisobutylketone and the like; nitriles such as acetonitrile, propanenitrile and the like; esters such as methyl acetate, ethyl acetate, n-propyl acetate, tert-butyl acetate and the like; haloalkanes such as dichloromethane, chloroform and the like; ethers such as dimethyl ether, methyl tertiary butyl ether, diisopropyl ether; dimethyl formamide; dimethylsulfoxide; terahydrofuran; dimethyl acetamide; dioxane; N-methylpyrrolidone; water or mixtures thereof.

Preferred solvents include ketones such as acetone, alcohols such as methanol, ethanol, 1-propanol, isopropanol, butanol; esters such as ethyl acetate; ethers such as dimethyl ether, methyl tertiary butyl ether; dimethyl formamide; dimethylsulfoxide; terahydrofuran; dimethyl acetamide; dioxane; N-methylpyrrolidone; water or mixtures thereof.

In one embodiment, the present invention provides a process for preparation of tofacitinib monoxalate wherein, tofacitinib is treated with oxalic acid in the presence of acetone as solvent.

Tofacitinib monoxalate, prepared above, may be purified. The purification may be performed by crystallization of tofacitinib monoxalate.

The crystallization may be performed using a suitable solvent. may include an alcohol such as methanol, ethanol, 1-propanol, isopropanol, 1-butanol, 2-butanol, 1-pentanol, 1-octanol and the like; a ketone such as acetone, propanone, methylisobutylketone and the like; a nitrile such as acetonitrile, propanenitrile and the like; an ester such as methyl acetate, ethyl acetate, n-propyl acetate, tert-butyl acetate and the like; a haloalkane such as dichloromethane, chloroform and the like; an ether such as dimethyl ether, isopropyl ether, methyl tert-butyl ether and the like; an aromatic hydrocarbon such as toluene and the like; a hydrocarbon such as n-hexane, n-heptane and the like; dimethyl formamide; dimethylsulfoxide; dimethyl acetamide; tetrahydrofuran; N-methylpyrrolidone; water; or mixtures thereof.

Preferred crystallization solvents include methanol, ethanol and isopropanol.

In one embodiment, the present invention provides a process for purification of tofacitinib monoxalate comprising crystallization of tofacitinib monoxalate from methanol.

Tofacitinib monoxalate, prepared above may be converted into tofacitinib monoditrate.

The conversion of tofacitinib monoxalate into tofacitinib mono citrate may be performed via tofacitinib or any other organic or inorganic acid addition salt tofacitinib. The conversion may be performed by treatment of tofacitinib monoxalate with a base to obtain tofacirinib. The base used may be an organic or inorganic base. The inorganic base may include an alkali or alkaline earth metal hydroxide, an alkali or alkaline earth metal carbonate and the like, for example sodium hydroxide, potassium hydroxide, sodium carbonate, potassium carbonate and the like. The organic base may be an amine base which may be a primary, secondary or tertiary amine. Examples of base include methylamine, ethylamine, triethylamine, propylamine, isopropylamine, di isopropylamine, tertiary butylamine and the like. Organic base also includes pyridine and DBU. Preferred bases include potassium carbonate, potassium hydroxide, sodium carbonate and sodium hydroxide.

The tofacitinib base so produced may be isolated as a solid or as oil. Tofacitinib isolated as oil may be recrystallized using a suitable solvent to obtain tofacitinib in solid form as discussed supra.

The tofacitinib, so produced, may be converted into mono citrate or other acid addition salts of tofacitinib as discussed supra.

In one embodiment, the present invention provides a process for preparation of tofacitinib or salts thereof, comprising use of tofacitinib monoxalate as an intermediate.

In one embodiment, the present invention provides a process for preparation of tofacitinib mono citrate, comprising use of tofacitinib monooxalate.

In one embodiment, the present invention provides a solvate of tofacitinib which solvate may be selected from the group consisting of methanol, n-propanol, isopropanol, dioxane, ethylacetate or methylenedichloride solvates.

In one embodiment, the present invention provides a process for preparing a solvate of tofacitinib which solvate may be selected from the group consisting of methanol, n-propanol, isopropanol, dioxane, ethylacetate or methylenedichloride solvate by process comprising recrystallizing or slurrying or triturating tofacitinib with methanol, n-propanol, isopropanol, dioxane, ethylacetate or methylenedichloride respectively.

In one embodiment, the present invention provides a process for preparation of tofacitinib monocitrate or tofacitinib hemictrate comprising use of methanol, n-propanol, isopropanol, dioxane, ethylacetate or methylenedichloride solvate of tofacitinib.

In one embodiment, the present invention provides a compound of Formula VII, as depicted in scheme 1 wherein, R is tosyl, which is represented by a compound of Formula VIIA.

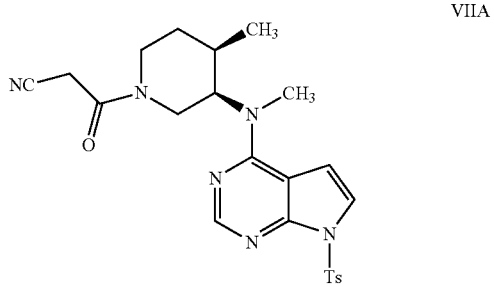 [SMILES: Cc1ccc(S(=O)(=O)n2ccc3c(N(C)[C@H]4CN(C(=O)CC#N)CC[C@H]4C)ncnc32)cc1]

VIIA

In one embodiment, the present invention provides a compound of Formula VII, as depicted in scheme 1 wherein, R is tertiary-butyloxy carbonyl.

The present invention provides a process for preparation of tofacitinib or salts thereof, comprising use of a compound of Formula VII.

The present invention provides a process for preparation of tofacitinib or salts thereof, comprising use of a compound of Formula VIIA.

The present invention provides a process for preparation of tofacitinib or salts thereof, comprising use of a compound of Formula VII, wherein R is tertiary-butyloxy carbonyl.

The present invention provides various organic and inorganic acid salts of compound of Formula VII. The acid addition salt may include organic acid addition salts and inorganic acid addition salts. The various organic and inorganic acid addition salts may be mono or diacid addition salts. The organic acid addition salts include mono and diacid addition salts of acids such as formic acid, oxalic acid, acetic acid, citric acid, tartaric acid, benzoic acid, lactic acid, malic acid, fumaric acid, succinic acid, gluconic acid, pamoic acid, methanesulfonic acid, benzenesulfonic acid and the like. The inorganic acid addition salts include mono and diacid addition salts of acids such as hydrochloric acid, hydrobromic acid, hydroiodic acid, nitric acid, phosphoric acid, sulfuric acid and the like.

The present invention provides various organic and inorganic acid salts of compound of Formula VIIA. The acid addition salt may include organic acid addition salts and inorganic acid addition salts. The various organic and inorganic acid addition salts may be mono or diacid addition salts. The organic acid addition salts include mono and diacid addition salts of acids such as formic acid, oxalic acid, acetic acid, citric acid, tartaric acid, benzoic acid, lactic acid, malic acid, fumaric acid, succinic acid, gluconic acid, pamoic acid, methanesulfonic acid, benzenesulfonic acid and the like. The inorganic acid addition salts include mono and diacid addition salts of acids such as hydrochloric acid, hydrobromic acid, hydroiodic acid, nitric acid, phosphoric acid, sulfuric acid and the like.

The present invention provides a process for preparation of tofacitinib or salts thereof, comprising use of the various aforementioned organic and inorganic salts of compound of Formula VII or VIIA.

The present invention provides a compound of Formula XV as depicted in Scheme 4, wherein R3 is C1-5 straight or branched alkyl.

The present invention provides a compound of Formula XV as depicted in Scheme 4, wherein R3 is methyl.

The present invention provides a process for preparation of tofacitinib or salts thereof, comprising use of a compound of Formula XV as depicted in Scheme 4, wherein R3 is C1-5 straight or branched alkyl.

The present invention provides a process for preparation of tofacitinib or salts thereof, comprising use of a compound of Formula XV as depicted in Scheme 4, wherein R3 is methyl.

The present invention provides a process for preparation of tofacitinib or salts thereof, comprising use of a compound of Formula XVI as depicted in Scheme 4.

The present invention provides a process for preparation of tofacitinib or salts thereof, comprising use of a compound of Formula XVI as depicted in Scheme 4.

EXAMPLES

Example 1: Preparation of methyl-(4-methylpyridin-3-yl)carbamate

To a suspension of 4-methylpyridine-3-amine (25 gm, 0.23 mol) in 125 ml dimethyl carbonate was added potassium t-butoxide lot wise at about 10-15° C. and the reaction mass was stirred for about 1 hr at about 10-15° C. The progress of the reaction was monitored by TLC. After completion of the reaction 100 ml of water was added to the reaction mass at about 10-15° C. The temperature of the mass was raised to about 20-25° C. and 100 ml of ethyl acetate was added. The mass was stirred for about 30 min and layers were separated. The ethyl acetate layer was washed with 50 ml water and concentrated under vacuum at about 50-55° C. to afford a residue. The residue was taken in di-isopropylether and stirred for about 1 hr at about 25-30° C. The precipitated solid was filtered and dried under vacuum at about 40-45° C. to afford 35 g methyl (4-methylpyridin-3-yl)carbamate.

Example 1A: Preparation of methyl-(4-methylpyridin-3-yl)carbamate 250 ml 25% sodium methoxide solution in methanol was distilled under vacuum and stripped out with toluene. 100 ml of toluene was charged to above reaction mass followed by 50 gm (0.46 mol) of 3-amino-4-methyl pyridine and 250 ml dimethyl carbonate. The reaction mass was heated to about 60-65° C. and maintained at this temperature for about 1.5-2.0 hrs. After completion of reaction excess of dimethyl carbonate was distilled under vacuum and methylene dichloride and water was added. The methylene dichloride layer was separated. Aq. layer was extracted twice with methylene dichloride. The combined methylene dichloride layer was washed with water. Organic layer was distilled under vacuum to afford a thick solid residue. Ethyl acetate was added to the residue under stirring at 55-60° C. and n-heptane was added slowly. After completion of addition, reaction mass was further cooled to room temperature and stirred for 5-6 hrs at same temperature. The precipitated solid was filtered and washed twice with heptane. The solid was dried under vacuum at 50-55° C. for 6-7 hrs to afford 60 gm methyl(4-methylpyridin-3-yl)carbamate. (HPLC purity>99.0%)

Example 2: Preparation of methyl-(4-methylpiperidin-3-yl)carbamate

To a solution of methyl (4-methylpyridin-3-yl)carbamate (33 gm, 0.19 mol) in 500 ml acetic acid was added 8.0 gm of 5% rhodium on alumina type 525 and the reaction mixture was hydrogenated in autoclave at about 70-75° C. under hydrogen pressure of about 7-8 kg/cm$^2$ for about 10 hrs. The progress of the reaction was monitored by TLC. After completion of the reaction the reaction mass was filtered through hyflow bed to remove the catalyst and the filtrate was concentrated under vacuum at about 60-70° C. to afford 30 gm methyl (4-methylpiperidin-3-yl)carbamate as a thick oil.

Example 2A: Preparation of methyl-(4-methylpiperidin-3-yl)carbamate

To a solution of methyl (4-methylpyridin-3-yl) carbamate (100 gm, 0.30 mol) in 600 ml ethanol and 100 ml acetic acid was added 30 gm of 5% rhodium on alumina and the reaction mixture was hydrogenated in autoclave at 75-80° C. under hydrogen pressure of 9-10 kg/cm$^2$ for 4-5 hrs. After completion of the reaction, the reaction mass was filtered. The filtrate was concentrated under vacuum at 60-70° C. The oily residue obtained was stripped out with ethyl acetate. The residue was dissolved in ethyl acetate and was gradually cooled to room temp (thick gray coloured slurry was obtained). n-heptane was added to the reaction mass and stirred for 8-9 hrs at room temperature. Reaction mass was further cooled to 10-15° C. and maintained for 2 hrs. The precipitated solid was filtered, washed with a mixture of ethylacetate and n-heptane (1:1, 100 ml) and finally with n-heptane. The filtered solid was dried under vacuum at 50-55° C. for to afford 65-70 gm methyl (4-methylpiperidin-3-yl)carbamate as a gray to light brown solid. (GC purity>96.0%; trans isomer<5%)

Example 3: Preparation of methyl-(1-trityl-4-methylpiperidin-3-yl)carbamate

To a solution of methyl-(4-methylpiperidin-3-yl)carbamate (6.5 gm, 0.016 mol) in 65 ml acetonitrile was added triethylamine (19.09 gm, 0.19 mol) and tritylchloride (13.67 gm, 0.049 mol) and the reaction mass was heated to reflux for about 10 hrs at about 65-70° C. The progress of the reaction was monitored by TLC. After completion of the reaction, the reaction mass was concentrated under vacuum at about 45-50° C. to afford a residue. The residue was taken in 100 ml ethylacetate and 50 ml water and stirred for about 30 min. The layers were separated. The aqueous layer was extracted with 50 ml of ethylacetate. The combined organic layers were concentrated under vacuum to afford a sticky solid, which was taken in di-isopropyl ether and stirred for about 30 min. the solid was filtered, washed with diisopropyl ether and dried under vacuum at about 40-45° C. to furnished 8.7 gm methyl (1-trityl-4-methylpiperidin-3-yl)carbamate as white solid.

Example 3A: Preparation of methyl-(1-trityl-4-methylpiperidin-3-yl)carbamate To a solution of methyl (4-methylpiperidin-3-yl)carbamate (100 gm, 0.581 mol) in 1000 ml acetonitrile was added triethylamine (147 gm, 1.452 mol) and trityl chloride (210.4 gm, 0.755 mol) and the reaction mass was heated at 65-70° C. for 4-6 hrs. The progress of the reaction was monitored by TLC. After completion of the reaction, the reaction mass was concentrated under vacuum at 45-50° C. to afford a residue. The residue was taken in methylene dichloride and water and stirred for about 30 min. The reaction mass was filtered and the layers were separated to obtain an aqueous layer 1 and an organic layer1. The organic layer1 was washed with water and layers were separated to obtain an aqueous layer 2 and organic layer2. The aqueous layers 1 and 2 were combined and extracted with methylene dichloride to obtain organic layer 3 and aqueous layer 3. The organic layers 2 and 3 were combined and concentrated under vacuum and stripped out with ethyl acetate to afford a thick slurry which was taken in ethyl acetate and stirred at 40-45° C. to form a uniform slurry. n-heptane was added slowly to above mass and was heated to 55-60° C. and maintained for 30 min. The mass was cooled to room temp and stirred for 5-6 hrs. The precipitated solid was filtered and washed with n-heptane. The solid was dried at 50-55° C. for 8-10 hrs to afford off-white solid. (HPLC purity>98.0%)

Example 4: Preparation of 1-trityl-N,4-dimethylpiperidin-3-amine hydrochloride Lithium aluminiumhydride (0.41 gm, 0.011 mol) was added lot wise to 20 ml tetrahydrofuran under nitrogen atmosphere and stirred for about 5 min. methyl-(1-trityl-4-methylpiperidin-3-yl)carbamate (0.09 gm, 0.0022 mol) was added lot wise and stirred for about 5 min. the reaction mass was heated to reflux at about 60-70° C. for about 4 hrs. The progress of the reaction was monitored by TLC. After completion of the reaction the reaction mass was cooled to about 0-5° C. and a solution of ammonium chloride in water (5 gm in 10 ml water) was added slowly and stirred for about 30 min. 25 ml of ethylacetate was added to the reaction mass and the temperature of the reaction mass was raised to about 25-30° C. and stirred for about 30 min. The layers were separated and the aqueous layer was extracted with 10 ml ethylacetate. The combined organic layer was dried over sodium sulfate and concentrated under vacuum at about 45-50° C. to afford 0.6 gm 1-trityll-N,4-dimethylpiperidin-3-amine as yellow oil. The oil was dissolved in 5 ml ethylacetate and the pH was adjusted to about 2-3 with ethylacetate hydrochloride and stirred for about 30 min at about 25-30° C. The precipitated solid was filtered and dried under vacuum at about 45-50° C. to afford 1-trityl-N,4-dimethylpiperidin-3-amine hydrochloride.

Example 4a: Preparation of 1-trityl-N,4-dimethylpiperidin-3-amine hydrochloride The process was followed as in example 4 till the preparation of -trityl-N,4-dimethylpiperidin-3-amine as yellow oil. The oil was crystallized in methanol and stirred for about 30 min at about 25-30° C. The precipitated solid was filtered and dried under vacuum at about 45-50° C. to afford 1-trityll-N,4-dimethylpiperidin-3-amine. A suspension of 1-trityl-N,4-dimethylpiperidin-3-amine (25 gm) in ethylacetate (250 ml) was cooled to about 5-10° C. and the pH of the reaction mass was adjusted to about 1-2 with slow addition of ethylacetate hydrochloride at same temperature. The reaction mass was stirred for about 1 hr at about 5-10° C. and the precipitated solid was filtered. The material was dried under vacuum at about 40-45° C. to afford 25 gm of 1-trityl-N,4-dimethylpiperidin-3-amine hydrochloride.

Example 4b: Preparation of 1-trityl-N,4-dimethylpiperidin-3-amine hydrochloride

To 400 ml sodium bis(2-methoxy-ethoxy)aluminium hydride (Vitride) a solution of methyl-(1-trityl-4-methylpiperidin-3-yl)carbamate (100 gm, 0.24 mol) in 500 ml THF was added slowly under nitrogen atmosphere. After completion of addition, the reaction mass was heated to 65-70° C. for 1.5-2.0 hrs. After completion of the reaction the reaction mass was cooled to 0-5° C. and water was added slowly through dropping addition funnel below 30° C. The reaction mass was gradually cooled to room temp and ethyl acetate was added to it. The reaction mass stirred for 30 min at same temperature and filtered through hyflo bed and bed was washed with ethyl acetate. The organic layer was separated and washed with water. The organic layer was distilled under vacuum at 45-50° C. and stripped out with methanol. Methanol was added to the mass and stirred for 4-5 hrs at room temperature. The precipitate was filtered and washed with methanol. The solid was dried at 50-55° C. for 5-6 hrs to afford the product as a white solid. (HPLC purity 99.5%)

Example 5: Preparation of di-p-toluyl-D-tartaric acid salt of (3R,4R)-1-trityl-N,4-dimethylpiperidin-3-amine

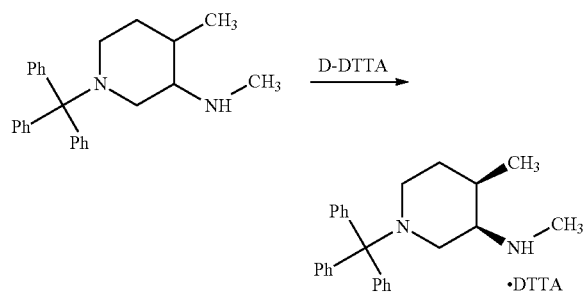

1-trityl-N,4-dimethylpiperidin-3-amine hydrochloride (1 gm, 0.0023 mol) was dissolved in 10 ml water and pH was adjusted to about 7-8 with aqueous potassium carbonate solution. The compound was extracted with ethylacetate and the organic layer was dried over sodium sulfate. To the solution D-DTTA (1.04 gm, 0.0023 mol) was added and the reaction mass was stirred for about 3 hrs at about 25-30° C. The precipitated solid was filtered and dried under vacuum at about 50-55° C. to afford 1.9 gm of di-p-toluyl-D-tartaric acid salt of (3R,4R)-1-trityl-N,4-dimethylpiperidin-3-amine.

Example 5a: Preparation of di-p-toluyl-D-tartaric acid salt of (3R,4R)-1-trityl-N,4-dimethylpiperidin-3-amine 1-trityl-N,4-dimethylpiperidin-3-amine (1 gm, 0.0023 mol) was dissolved in acetone and D-DTTA (1.04 gm, 0.0023 mol) was added. The reaction mass was stirred for about 3 hrs at about 25-30° C. The precipitated solid was filtered and dried under vacuum at about 50-55° C. to afford 1.9 gm of D-DTTA salt of (3R,4R)-1-trityl-N,4-dimethylpiperidin-3-amine.

Example 5b: Preparation of di-p-toluyl-D-tartaric acid salt of (3R,4R)-1-trityl-N,4-dimethylpiperidin-3-amine To a suspension of 1-trityl-N,4-dimethylpiperidin-3-amine hydrochloride (100 gm, 0.27 mol) in 10% aqueous methanol (1000 ml) was added D-DTTA (52.14 gm, 0.135 mol) and the mass was stirred for 1 hr at room temperature. The reaction mass was heated to 65-70° C. for 2 hrs and then gradually cooled to room temperature and stirred for 5-6 hrs. The solid was filtered and washed with 10% aqueous methanol. The wet cake obtained was taken in 10% aqueous methanol and heated to 65-70° C. for 2 hrs. The mass was gradually cooled to room temperature and stirred for 5-6 hrs at same temperature. The suspension was filtered and washed with 10% aqueous methanol. The filtered solid was dried at 50-55° C. for 5-6 hrs to afford the product as a white solid. (Chiral purity 99.65%, (S,S) isomer content 0.35%)

Example 5c: Preparation of di-p-toluyl-L-tartaric acid salt of (3S,4S)-1-trityl-N,4-dimethylpiperidin-3-amine 1-trityl-N,4-dimethylpiperidin-3-amine hydrochloride was dissolved in water and pH was adjusted to about 7-8 with aqueous potassium carbonate solution. The compound was extracted with ethylacetate and the organic layer was dried over sodium sulfate. To the solution L-DTTA was added and the reaction mass was stirred. The precipitated solid was filtered and dried under vacuum to afford of di-p-toluyl-L-tartaric acid salt of (3S,4S)-1-trityl-N,4-dimethylpiperidin-3-amine.

Example 6: Purification of di-p-toluyl-D-tartaric acid salt of (3R,4R)-1-trityl-N,4-dimethylpiperidin-3-amine 1 gm D-DTTA salt of (3R,4R)-1-trityl-N,4-dimethylpiperidin-3-amine was dissolved in a mixture of ethanol and water (80:20) at about 60-70° C. to get a slurry. The solution was then cooled to 25-30° C. and stirred for 3 hrs at same temperature. The precipitated solid was filtered and stirred under vacuum at about 50-55° C. to afford pure 0.8 gm of pure di-p-toluyl-D-tartaric acid salt of (3R,4R)-1-trityl-N,4-dimethylpiperidin-3-amine.

Example 6a: Preparation of (3R,4R)-1-trityl-N,4-dimethylpiperidin-3-amine

D-DTTA salt of (3R,4R)-1-trityl-N,4-dimethylpiperidin-3-amine, as prepared in example 6, was taken in water and pH was adjusted to about 8-10 using aqueous potassium carbonate solution. The product was extracted with dichloromethane and the organic layer was concentrated. The obtained residue was crystallized in methanol to afford pure (3R,4R)-1-trityl-N,4-dimethylpiperidin-3-amine.
The product may further be converted to various salts.

Example 6b: Preparation of (3R,4R)-1-trityl-N,4-dimethylpiperidin-3-amine

The pH of the suspension of D-DTTA salt of (3R,4R)-1-trityl-N,4-dimethylpiperidin-3-amine (50 gm) in 500 ml water and ethyl acetate (1:1) was adjusted to 9-10 with aqueous potassium carbonate solution (25 g in 50 ml water) and the mass was stirred for 1 hr. The layers were separated and the aqueous layer was extracted 1 ethyl acetate. The combined organic layer was washed with water and distilled under vacuum at 50-55° C. to afford a residue. The residue was stripped out with methanol, then taken in methanol and stirred for 4-5 hrs at room temperature. The reaction mass was filtered and washed with chilled methanol. The obtained solid was dried at 50-55° C. for 5-6 hrs to afford the product as a white solid. (HPLC purity 99.9%, Chiral purity 99.85%; (S,S) isomer 0.15%).

Example 7: Preparation of 2,4-dichloro-7-[(4-methylphenyl)sulfonyl]-7H-pyrrolo[2,3-d]pyrimidine To a suspension of 2,4-dichloro-7H-pyrrolo[2,3-d]pyrimidine (1 g, 0.005 mol) and toluene sulfonylchloride (1.3 gm, 0.007) in 10 ml acetone cooled to about 0-5° C., a solution of sodium hydroxide in water (0.32 gm in 4 ml water) was added slowly at about 0-5° C. The temperature of the reaction mass was raised to 25-30° C. and stirred for 2-3 hrs. The progress of the reaction was monitored by TLC. After completion of the reaction the reaction mass was filtered and washed with a mixture of acetone and water. The solid was dried under vacuum at about 50-55° C. for about 10 hrs to afford 1.5 gm of 2,4-dichloro-7-[(4-methylphenyl)sulfonyl]-7H-pyrrolo[2,3-d]pyrimidine as yellow colored solid. (HPLC purity>98.0%)

Example 8: Preparation of Compound of Formula V (Wherein $R_1$=Trityl and R=Tosyl)

To a solution of 2,4-dichloro-7-[(4-methylphenyl)sulfonyl]-7H-pyrrolo[2,3-d]pyrimidine (0.78 gm, 0.0023 mol) in 5 ml dimethyl formamide was added (3R,4R)-1-trityl-N,4-dimethylpiperidin-3-amine(dihydrochloride (1 gm, 0.0023 mol) and potassium carbonate (1.6 gm, 0.011) at about 25-30° C. The temperature of the reaction mass was raised to about 70-75° C. and stirred for 10 hrs at about 70-75° C. The progress of the reaction was monitored by TLC. After completion of the reaction the reaction mass was cooled to about 25-30° C. and diluted with 10 ml water and the product was extracted with 20 ml ethyl acetate. The aqueous layer was extracted with 10 ml ethyl acetate and the combined organic layer was washed with 10 ml water and dried over sodium sulfate. The organic layer was concentrated under vacuum at about 45-50° C. to afford the product.

Example 8-I: Preparation of Compound of Formula V (Wherein $R_1$=Trityl and R=Tosyl)

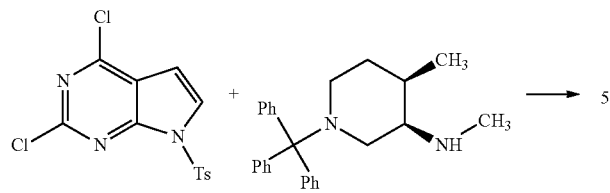

To a solution of 2,4-dichloro-7-[(4-methylphenyl)sulfonyl]-7H-pyrrolo[2,3-d]pyrimidine (41 gm, 0.1198 mol) in 350 ml dimethyl formamide and 150 ml acetonitrile was added (3R,4R)-1-trityl-N,4-dimethylpiperidin-3-amine (50 gm, 0.135 mol), potassium carbonate (91.25 gm, 0.66 mol) at about 25-30° C. The temperature of the reaction mass was raised to about 70-75° C. and stirred for 6 hrs at about 70-75° C. The progress of the reaction was monitored by TLC. After completion of the reaction, the reaction mass was cooled to about 25-30° C. and reaction mass was slowly added to the water to afford off white solid. Reaction mass stirred for 2 hrs and filtered to afford 70 gm product. (HPLC purity 80.0%)

Example 8-II: Preparation of Compound of Formula V (Wherein $R_1$=Trityl and R=Tosyl)

To a solution of 2,4-dichloro-7-[(4-methylphenyl)sulfonyl]-7H-pyrrolo[2,3-d]pyrimidine (41 gm, 0.1198 mol) in 350 ml dimethyl formamide and 150 ml acetonitrile was added (3R,4R)-1-trityl-N,4-dimethylpiperidin-3-amine (50 gm, 0.135 mol), potassium carbonate (91.25 gm, 0.66 mol) at about 25-30° C. The temperature of the reaction mass was raised to about 70-75° C. and stirred for 6 hrs at about 70-75° C. After completion of the reaction, the reaction mass was cooled to about 25-30° C. and was slowly added to water. The precipitated solid was stirred and filtered. The filtered solid was reacted with aqueous sodium hydroxide (12.36 gm, 0.309 mol) in acetone at 55-60° C. till completion of the reaction. The progress of the reaction was monitored by TLC. After completion of the reaction, the reaction mass was added slowly to water at 20-25° C. and stirred for 2 hrs. Reaction mass filtered to afford 54 gm product. (HPLC purity 80.0%)

Example 8a: Preparation of Compound of Formula VA (Wherein R=Tosyl)

A solution of compound prepared in example 8 or 8-I (1 gm, 0.0015 mol) in dichloromethane was added dropwise to trifluroacetic acid at 5-10° C. and stirred for 3 hrs. The progress of the reaction was monitored by TLC. After completion of the reaction, the reaction mass was concentrated and pH was adjusted to about 9-10 with ammonium hydroxide and the product was extracted with dichloromethane. The dichloromethane layer was concentrated to afford an oil which was taken in acetone and pH was adjusted to about 1-2 with dilute hydrochloric acid. The precipitated solid was filtered off, the filtrate was treated with water and pH was adjusted to about 9-10 with ammonium hydroxide. The product was extracted with dichloromethane and was concentrated to afford the product.

Example 8a-I: Preparation of Compound of Formula VAA (Wherein $R_1$=Trityl)

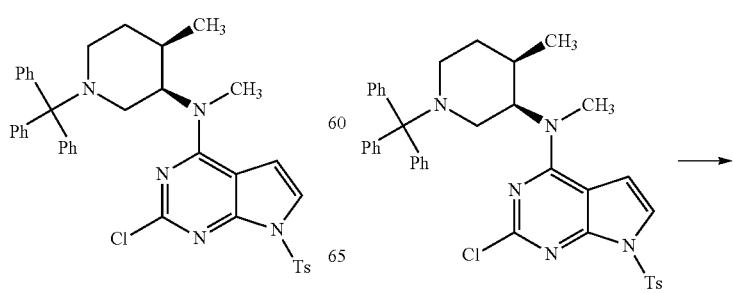

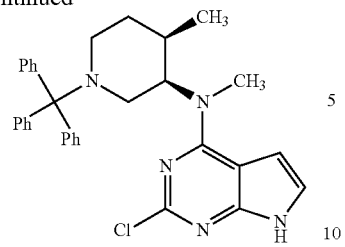

A solution of compound prepared in example 8 or 8-I (70 gm 0.103 mol) and 560 ml acetone and aqueous sodium hydroxide (12.36 gm, 0.309 mol) was added to it and the reaction mass was heated to about 55-60° C. till completion of the reaction. The progress of the reaction was monitored by TLC. After completion of the reaction, the reaction mass was added slowly to water at 20-25° C. and stirred for 2 hrs. Reaction mass filtered to afford 54 gm product. (HPLC purity 80.0%)

Example 8a-II: Preparation of Compound of Formula VAA (Wherein $R_1$=Trityl)

To a solution of 2,4-dichloro-7-[(4-methylphenyl)sulfonyl]-7H-pyrrolo[2,3-d]pyrimidine (41 gm, 0.1198 mol) in 350 ml dimethyl formamide and 150 ml acetonitrile was added (3R,4R)-1-trityl-N,4-dimethylpiperidin-3-amine (50 gm, 0.135 mol), potassium carbonate (91.25 gm, 0.66 mol) at about 25-30° C. The temperature of the reaction mass was raised to about 70-75° C. and stirred for 6 hrs at about 70-75° C. After completion of the reaction, the reaction mass was cooled to about 25-30° C. and was slowly added to water. The precipitated solid was stirred and filtered. The filtered solid was reacted with aqueous sodium hydroxide (12.36 gm, 0.309 mol) in acetone at 55-60° C. till completion of the reaction. The progress of the reaction was monitored by TLC. After completion of the reaction, the reaction mass was added slowly to water at 20-25° C. and stirred for 2 hrs. Reaction mass filtered to afford 54 gm product. (HPLC purity 80.0%)

Example 8b: Preparation of N-methyl-N-[(3R,4R)-4-methylpiperidin-3-yl]-7H-pyrrolo[2,3-d]pyrimidin-4-amine (compound of Formula VB)

A solution of compound prepared in example 8a in acetone was treated with aqueous sodium hydroxide and the reaction mass was heated to about 50-55° C. till completion of the reaction. The progress of the reaction was monitored by TLC. After completion of the reaction the reaction mass was concentrated to afford the product.

Example 8b-I: Preparation of N-methyl-N-[(3R,4R)-4-methylpiperidin-3-yl]-7H-pyrrolo[2,3-d]pyrimidin-4-amine (compound of Formula VB)

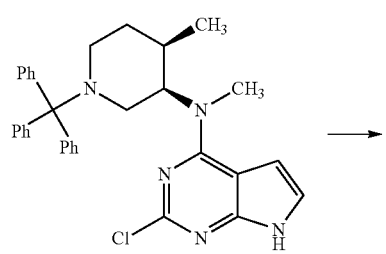

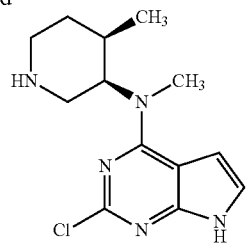

A solution of compound prepared in example 8a-I or 8a-II (54 gm, 0.0015 mol) in methylene dichloride was added drop wise to 54 ml trifluroacetic acid at 5-10° C. and stirred for 1 hr. The progress of the reaction was monitored by TLC. After completion of the reaction, methylene dichloride and water were added to the reaction mass and pH was adjusted to about 9-10 with potassium carbonate. The precipitated solid was filtered, to afford 25 gm of product which was further purified in ethyl acetate.

Example 8b-II: Preparation of N-methyl-N-[(3R,4R)-4-methylpiperidin-3-yl]-7H-pyrrolo[2,3-d]pyrimidin-4-amine (compound of Formula VB)

A solution of compound prepared in example 8a-I or 8a-II (160 gm, 0.306 mol) in 960 ml dichlorormethane was added dropwise to 80 ml trifluroacetic acid and 320 ml MDC at 5-10° C. and stirred for 1 hrs. The progress of the reaction was monitored by TLC. After completion of the reaction, dichlorormethane and water were added to the reaction mass and pH was adjusted to about 9-10 with potassium carbonate. The precipitated solid was filtered, to afford 75 gm of crude product which was further purified in ethyl acetate: Heptane. (HPLC purity>97.0%)

Example 8c: Preparation of Compound of Formula XII

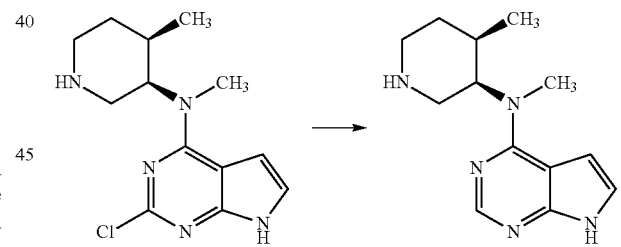

A solution of compound prepared in example 8b or 8b-I or 8b-II in ethanol and acetic acid was hydrogenated using palladium hydroxide on carbon under hydrogen pressure of about 7-8 kg/cm² at about 70-75° C. for about 4 hrs. The progress of the reaction was monitored by TLC. After completion of the reaction, the reaction mass was cooled to about 25-30° C. and then filtered through hyflo to remove palladium hydroxide on carbon. The filtrate was concentrated to afford a residue which was taken in water and pH was adjusted to about 9-10 using aqueous potassium carbonate. The product was extracted with dichloromethane and the organic layer was concentrated to afford the product.

Example 8d: Preparation of Compound of Formula XII

To a solution of the product prepared in example 8b or 8b-I or 8b-II (25 gm, 0.089 mol) in methanol, was added 0.25 gm of 10% Pd(OH)$_2$/C and the mixture was hydrogenated under hydrogen pressure of 7-8 kg at about 50-55° C. for about 4 hrs. The progress of the reaction was monitored by TLC. After completion of the reaction the reaction mass was cooled to about 25-30° C. and then filtered to remove Pd(OH)$_2$/C. The filtrate was concentrated under vacuum to afford 25 gm of N-methyl-N-[(3R,4R)-4-methylpiperidin-3-yl]-7H-pyrrolo[2,3-d]pyrimidin-4-amine.

Example 8e: Preparation of N-methyl-N-[(3R,4R)-4-methylpiperidin-3-yl]-7H-pyrrolo[2,3-d]pyrimidin-4-amine (compound of Formula XII)

To a solution of the product prepared in example 8b or 8b-I or 8b-II (10 gm, 0.035 mol) in 200 ml methanol was added 0.1 gm of 10% Pd/C and the mixture was hydrogenated under hydrogen pressure of 8-10 kg at about 50-55° C. for about 4-5 hrs. The progress of the reaction was monitored by TLC. After completion of the reaction the reaction mass was cooled to about 25-30° C. and then filtered to remove Pd/C. The filtrate was concentrated under vacuum to afford N-methyl-N-[(3R,4R)-4-methylpiperidin-3-yl]-7H-pyrrolo[2,3-d]pyrimidin-4-amine. (HPLC purity>97.0%)

Example 8f Preparation of N-methyl-N-[(3R,4R)-4-methylpiperidin-3-yl]-7H-pyrrolo[2,3-d]pyrimidin-4-amine (compound of Formula XII)

To a solution of the product prepared in example 8b or 8b-I or 8b-II (05 gm, 0.0178 mol) in 100 ml methanol was added 00.5 gm of 10% Pd/C and 2.72 gm (0.0178 mol) DBU the mixture was hydrogenated under hydrogen pressure of 8-10 kg at about 50-550 C for about 4-5 hrs. The progress of the reaction was monitored by TLC. After completion of the reaction the reaction mass was cooled to about 25-30° C. and then filtered to remove Pd/C. The filtrate was concentrated under vacuum to afford N-methyl-N-[(3R,4R)-4-methylpiperidin-3-yl]-7H-pyrrolo[2,3-d]pyrimidin-4-amine. (HPLC purity>97.0%)

Example 9: Preparation of N-methyl-N-[(3R,4R)-4-methylpiperidin-3-yl]-7H-pyrrolo[2,3-d]pyrimidin-4-amine (compound of Formula XII)

To a solution of the product prepared in example 8 (1 gm, 0.0015 mol) in methanol was added 0.1 gm of 10% Pd/C and the mixture was hydrogenated under hydrogen pressure of 5 kg at about 45-55° C. for about 10 hrs. The progress of the reaction was monitored by TLC. After completion of the reaction the reaction mass was cooled to about 25-30° C. and then filtered through hyflo to remove Pd/C. The filtrate was further treated with aqueous sodium hydroxide solution at reflux temperature. The progress of the reaction was monitored by TLC. After completion of the reaction the reaction mass was concentrated under vacuum to afford N-methyl-N-[(3R,4R)-4-methylpiperidin-3-yl]-7H-pyrrolo[2,3-d]pyrimidin-4-amine.

Example 10: Preparation of Tofacitinib

To a solution of cyanoacetic acid in methylene dichloride was added N-methylmorpholine at about 25-30° C. and stirred for about 10 min at about 25-30° C. The reaction mass was cooled to about 0-5° C. and isobutylchloroformate was added. The reaction mass was stirred for about 30 min at about 0-5° C. and a solution of N-methyl-N-[(3R,4R)-4-methylpiperidin-3-yl]-7H-pyrrolo[2,3-d]pyrimidin-4-amine in methylene dichloride was added slowly at about 0-5° C. The reaction mass was stirred for about 30 minutes. After completion of reaction the reaction mass was quenched with water and organic layer concentrated to afford 3-{(3R,4R)-4-methyl-3-[methyl(7H-pyrrolo[2,3-d]pyrimidin-4-yl)amino]piperidin-1-yl}-3-oxopropanenitrile (Tofacitinib). Tofacitinib so produced, was in the form of oil.

Example 11: Preparation of Tofacitinib

To a solution of cyanoacetic acid in methylene chloride was added oxalyl chloride and 1 drop of dimethylformamide. The reaction was stirred at about 20-25° C. and monitored using TLC. After completion of the reaction, the reaction mass was concentrated to dryness to afford cyanoacetyl chloride.

To a solution of N-methyl-N-[(3R,4R)-4-methyl piperidin-3-yl]-7H-pyrrolo[2,3-d]pyrimidin-4-amine in dichloromethane was added cyanoacetylchloride, prepared above, slowly at about 0-5° C. The reaction mass was stirred till completion of reaction. After completion of reaction, the reaction mass was quenched with water and organic layer was concentrated to afford 3-{(3R,4R)-4-methyl-3-[methyl (7H-pyrrolo[2,3-d]pyrimidin-4-yl)amino]piperidin-1-yl}-3-oxopropanenitrile (Tofacitinib free base) as thick oil.

Example 11a: Preparation of Tofacitinib

To a solution of compound of Formula XII (39 gm, 0.06 mol) in 390 ml THF was added 60.5 gm 1,8-Diazabicyclo [5.4.0]undec-7-ene (DBU) and 78.76 gm methyl cyanoacetate. Reaction mass stirred at 25-30° C. After completion of the reaction, the reaction mass was concentrated under vacuum at 30-35° C. Ethyl acetate and water were charged to the residue and pH was adjusted to 1-2 with aqueous HCl. The mass was stirred and layers were separated. Aqueous layer was washed with ethyl acetate. pH of aqueous layer adjusted to 9-10 with potassium carbonate solution and product was extracted with methylene dichloride. Organic layer concentrated under vacuum to afford thick oil (Tofacitinib free base) which was titturated with methanol to afford tofacitinib free base as a solid. (HPLC purity→99.0%)

Example 11b: Preparation of Tofacitinib

To a solution of XII (15 gm, 0.06 mol) in 150 ml ethanol was added 24.1 gm and 31.3 gm methyl cyano acetate. Reaction mass stirred at 25-30° C. After completion of the reaction, the reaction mass was concentrated under vacuum at 45-50° C. Ethyl acetate and water were charged to the residue and pH was adjusted to 1-2 with aqueous HCl. The mass was stirred and layers were separated. Aqueous layer was washed with ethyl acetate. pH of aqueous layer adjusted to 9-10 with potassium carbonate solution and product was extracted with methylenedichloride. Organic layer concentrated under vacuum to afford thick oil (Tofacitinib free base).

Example 12: Preparation of Tofacitinib Mono-Oxalate

Tofacitinib, prepared as oil, as in example 10, 11 or 11b was taken in acetone and a solution of oxalic acid was added slowly to it at room temperature. Precipitation occurred. The suspension was stirred for about 2 hrs and filtered to afford tofacitinib monooxalate. The monoxalate salt was purified by crystallization in methanol to afford pure oxalate salt.

Example 13: Preparation of Tofacitinib Citrate

Tofacitinib, prepared as oil, as in 10, 11 or 11b was taken in acetone and a solution of citric acid was slowly added to it at room temperature. The precipitated solid was stirred for about 2 hours and filtered to afford tofacitinib citrate.

Example 14: Preparation of Tofacitinib Citrate

The pure tofacitinib monooxalate salt, prepared in example 12, was taken in water and pH of the solution was adjusted to about 8-10 with aqueous potassium carbonate and the product was extracted with dichloromethane. The organic layer was concentrated under vacuum to afford an oil which was taken in acetone and a solution of citric acid was added slowly to it at room temperature. Precipitation occurred. The suspension was stirred for about 2 hrs and filtered to afford tofacitinib citrate.

Example 15: Preparation of Tofacitinib

To a solution of compound of Formula XII (15 gm, 0.06 mol) in 150 ml ethanol was added 24.1 gm 1,8-Diazabicyclo [5.4.0]undec-7-ene (DBU) and 31.3 gm methyl cyano acetate. Reaction mass stirred at 25-30° C. After completion of the reaction, the reaction mass was concentrated under vacuum at 45-50° C. To the residue obtained, ethyl acetate and water were charged and pH adjusted to 1-2 with aqueous HCl. Mass was stirred and layers separated. Aqueous layer was washed with ethyl acetate. pH of aqueous layer adjusted to 9-10 with potassium carbonate solution and the product extracted with methylene dichloride.

Example 15a: Preparation of Tofacitinib Hemicitrate

To a solution of compound of Formula XII (39 gm, 0.06 mol) in 390 ml THF was added 60.5 gm 1,8-Diazabicyclo [5.4.0]undec-7-ene (DBU) and 78.76 gm methyl cyanoacetate. Reaction mass stirred at 25-30° C. After completion of the reaction, the reaction mass was concentrated under vacuum at 30-35° C. Ethyl acetate and water were charged to the residue and pH was adjusted to 1-2 with aqueous HCl. The mass was stirred and layers were separated. Aqueous layer was washed with ethyl acetate. pH of aqueous layer adjusted to 9-10 with potassium carbonate solution and product was extracted with methylene dichloride. Organic layer was concentrated under vacuum to afford thick oil which was triturated with methanol to afford 26 gm tofacitinib as a solid. (HPLC purity>99.0%).
5 gm (0.016 mol) tofacitinib was taken in 50 ml ethanol and heated to reflux. 1.54 gm (0.008 mol) citric acid was added to the above reaction mass and reflux continued for 2 hrs. The reaction mass was gradually cooled to room temperature, stirred and filtered and dried to afford tofacitinib hemicitrate. (Citrate content 23.02%)

Example 15b: Preparation of Tofacitinib Hemicitrate 5 gm tofacitinib was taken in 100 ml methanol:water (7:3) and heated to reflux and 1.54 gm of citric acid was added to the above reaction mass and reflux contd. for 2 hrs. The reaction mass was gradually cooled to room temperature, stirred and filtered and dried to afford tofacitinib hemicitrate.

Example 16: Purification of Tofacitinib Monocitrate

Crude tofacitinib monocitrate (29 gm, HPLC purity 98%) was dissolved in 465 ml acetonitrile:water (7:3) at 75-80° C. to get a clear solution which was gradually cooled to room temp. and stirred and then filtered to afford 25 gm of pure tofacitinib citrate (HPLC purity 99.8%).

We claim:
1. A process for the preparation of a compound of Formula V-II

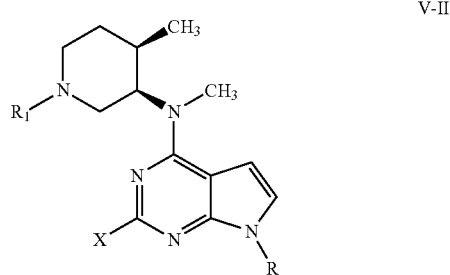

wherein, $R_1$ is trityl; R is hydrogen or tosyl; and X is a halogen; wherein the process comprises:
(a) reacting a compound of Formula IV wherein $R_1$ is trityl;

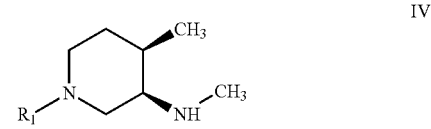

with a compound of Formula III-I wherein X is a halogen and R is tosyl,

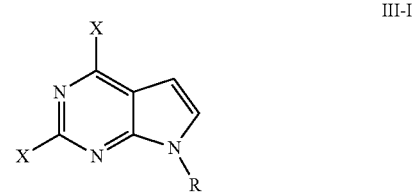

to form a compound of Formula V-II wherein $R_1$ and X have the aforestated meanings; and

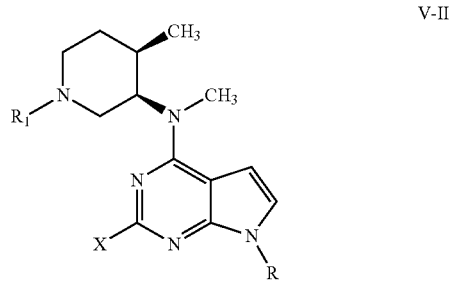

(b) optionally, deprotecting the compound of Formula V-II so obtained to form a compound of Formula V-II wherein at least one of R or $R_1$ is hydrogen and X is a halogen.

2. The process according to claim 1, for the preparation of the compound of Formula V-II and salts thereof, wherein each of R and $R_1$ is hydrogen and X is a halogen; and salts thereof,

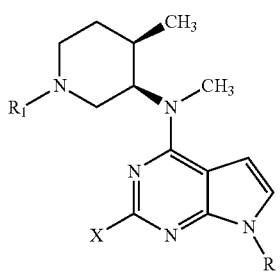

V-II wherein the deprotecting step (b) comprises (a)
  (i) converting the compound of Formula V-II, wherein $R_1$ is trityl; R is tosyl; and X is a halogen, into a compound of Formula V-II wherein $R_1$ is trityl; R is hydrogen and X is a halogen; followed by
  (ii) converting the compound of Formula V-II so obtained into a compound of Formula V-II wherein each of R and $R_1$ is hydrogen; and X is a halogen; or (b)
  (i) converting the compound of Formula V-II, wherein $R_1$ is trityl; R is tosyl; and X is a halogen, into a compound of Formula V-II wherein $R_1$ is hydrogen; R is tosyl and X is a halogen, followed by
  (ii) converting the compound of Formula V-II so obtained into a compound of Formula V-II wherein each of R and $R_1$ is hydrogen; and X is a halogen or (c) converting compound of Formula V-II, wherein $R_1$ is trityl; R is tosyl; and X is a halogen, directly into a compound of Formula V-II wherein each of R and $R_1$ is hydrogen and X is a halogen, in a single step.

3. The process according to claim 2 wherein deprotection in step (b)(a)(i) is performed using a base and deprotection in step (b)(a)(ii) is performed using an acid or by hydrogenation.

4. The process according to claim 2 wherein deprotection in step (b)(b)(i) is performed using an acid and deprotection in step (b)(b)(ii) is performed using a base.

5. The process according to claim 2 wherein deprotection in step (b)(c) is performed using an acid or base or by hydrogenation.

6. The process according to claim 2 further comprising dehalogenation of the compound of Formula V-II, wherein each of R and $R_1$ is hydrogen and X is a halogen, to form a compound of Formula XII followed by conversion of the compound of Formula XII into tofacitinib

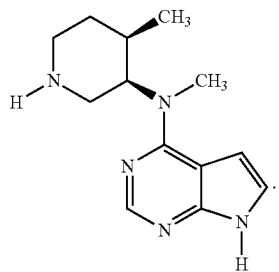

XII

7. The process according to claim 1, wherein the compound of Formula IV in which $R_1$ is trityl

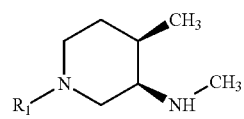

IV is prepared by the process comprising:
  (a) converting a compound of Formula XIV to a compound of Formula XV-I wherein $R_1$ is trityl, and $R_3$ is a $C_1$ to $C_5$ straight or branched chain alkyl;

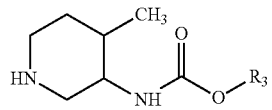

XIV

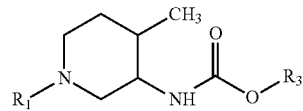

XV-I (b) converting the compound of Formula XV-I so obtained to a compound of Formula XVI-I wherein $R_1$ is trityl; followed by

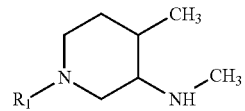

XVI-I (c) resolution of the compound of Formula XVI-I so obtained.

8. The process according to claim 7 wherein $R_3$ is methyl.

9. The process of claim 6, further comprising the steps of:
  treating tofacitinib with citric acid in a suitable solvent to obtain tofacitinib monocitrate; and
  recrystallizing tofacitinib monocitrate from a mixture of acetonitrile and water.

10. The process according to claim 1, wherein in step b, the compound of Formula V-II, in which $R_1$ is trityl; R is tosyl; and X is a halogen, is deprotected with a base to obtain a compound of Formula V-II, wherein $R_1$ is trityl; R is hydrogen and X is a halogen.

11. The process according to claim 1, wherein in step b, the compound of Formula V-II, in which $R_1$ is trityl; R is tosyl; and X is a halogen, is deprotected with an acid to obtain a compound of Formula V-II, wherein $R_1$ is hydrogen; R is tosyl, and X is a halogen.

12. The process according to claim 7, wherein the compound of Formula IV

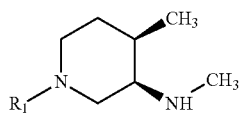

IV wherein $R_1$ is trityl, is thereafter converted to tofacitinib or salts thereof.

13. The process of claim 1, wherein the compound of Formula V-II, wherein $R_1$ is hydrogen or trityl and R is hydrogen or tosyl, represented by a compound of Formula V,

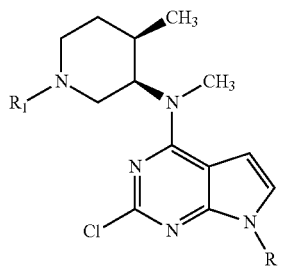

V is thereafter converted to tofacitinib or salts thereof.

14. A process for the preparation of a compound of Formula V-II

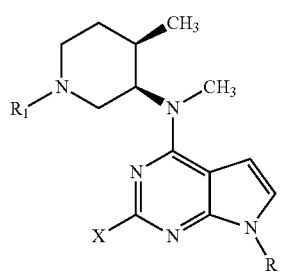

V-II wherein, $R_1$ is hydrogen or trityl; R is hydrogen or tosyl; and X is a halogen; wherein the process comprises:

(a) reacting a compound of Formula IV wherein $R_1$ is trityl;

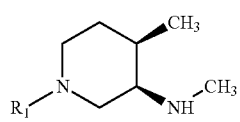

IV with a compound of Formula III-I wherein X is a halogen and R is tosyl,

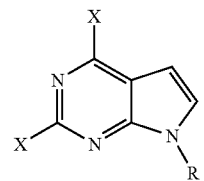

III-I to form a compound of Formula V-II wherein $R_1$ and X have the aforestated meanings; and

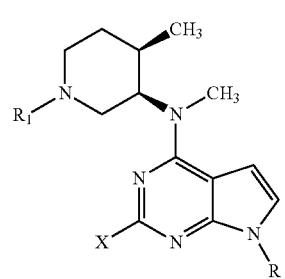

V-II (b) deprotecting the compound of Formula V-II so obtained to form a compound of Formula V-II wherein at least one of R or $R_1$ is hydrogen and X is a halogen.

15. The process according to claim 14, further comprising dehalogenation of the compound of Formula V-II, wherein each of R and $R_1$ is hydrogen and X is a halogen, to form a compound of Formula XII followed by conversion of the compound of Formula XII into tofacitinib

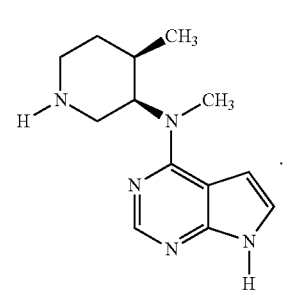

XII

16. The process of claim 15, further comprising the steps of:
treating tofacitinib with citric acid in a suitable solvent to obtain tofacitinib monocitrate; and
recrystallizing tofacitinib monocitrate from a mixture of acetonitrile and water.

17. The process according to claim 14, wherein in step (b), the compound of Formula V-II, in which $R_1$ is trityl; R is tosyl; and X is a halogen, is deprotected with a base to obtain a compound of Formula V-II, wherein $R_1$ is trityl; R is hydrogen and X is a halogen.

18. The process according to claim 17, further comprising converting the compound of Formula V-II, in which $R_1$ is trityl; R is hydrogen and X is a halogen, into tofacitinib.

19. The process according to claim 14, wherein in step (b), the compound of Formula V-II, in which $R_1$ is trityl; R is tosyl; and X is a halogen, is deprotected with an acid to obtain a compound of Formula V-II, wherein $R_1$ is hydrogen; R is tosyl, and X is a halogen.

20. The process according to claim 19, further comprising converting the compound of Formula V-II, in which $R_1$ is hydrogen; R is tosyl, and X is a halogen, into tofacitinib.

* * * * *